US011639943B2

(12) United States Patent
Imai et al.

(10) Patent No.: US 11,639,943 B2
(45) Date of Patent: May 2, 2023

(54) AUTOMATIC ANALYSIS DEVICE

(71) Applicant: HITACHI HIGH-TECH CORPORATION, Tokyo (JP)

(72) Inventors: Kenta Imai, Tokyo (JP); Hiroya Umeki, Tokyo (JP); Shunsuke Sasaki, Tokyo (JP); Yoshihiro Yamashita, Tokyo (JP); Taku Sakazume, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 434 days.

(21) Appl. No.: 16/641,349

(22) PCT Filed: Jun. 21, 2018

(86) PCT No.: PCT/JP2018/023577
§ 371 (c)(1),
(2) Date: Feb. 24, 2020

(87) PCT Pub. No.: WO2019/053991
PCT Pub. Date: Mar. 21, 2019

(65) Prior Publication Data
US 2020/0241029 A1 Jul. 30, 2020

(30) Foreign Application Priority Data
Sep. 13, 2017 (JP) .............................. JP2017-175685

(51) Int. Cl.
*G01N 35/10* (2006.01)
*G01N 33/49* (2006.01)
(Continued)

(52) U.S. Cl.
CPC ......... *G01N 35/1002* (2013.01); *G01N 33/49* (2013.01); *G01N 33/493* (2013.01); *G01N 35/04* (2013.01); *G01N 2035/00346* (2013.01)

(58) Field of Classification Search
CPC ..... G01N 35/1002; G01N 2035/00346; G01N 33/493; G01N 21/76; G01N 35/04; G01N 33/49
See application file for complete search history.

(56) References Cited

U.S. PATENT DOCUMENTS 5,334,349 A     8/1994   Kelln et al.
5,420,408 A     5/1995   Weyrauch et al.
(Continued)

FOREIGN PATENT DOCUMENTS

EP         0216026 A1    4/1987
JP         S63-066466 A   3/1988
(Continued)

OTHER PUBLICATIONS

Examination Report dated Mar. 25, 2022 in Indian Application No. 202117047988.
(Continued)

*Primary Examiner* — Shogo Sasaki
(74) *Attorney, Agent, or Firm* — Miles & Stockbridge, P.C.

(57) ABSTRACT

There is provided an automatic analysis device that can easily realize introduction and replacement of additional reagents in operation even in a small-scale configuration. The automatic analysis device includes a reagent dispensing mechanism 107 that dispenses a reagent from a reagent container 113 containing a reagent, and a normal reagent storage portion 130 that stores a reagent container and an additional reagent storage portion 111. The normal reagent storage portion 130 is positioned in a normal movable area 132, which is a portion of a movable area 131 of the reagent dispensing mechanism 107 and the additional reagent storage portion 111 is positioned in an area excluding the normal movable area 132 in the movable area 131 of the reagent dispensing mechanism 107. The reagent dispensing mecha- (Continued)

nism 107 performs an access operation in the normal movable area 132 in the normal operation and performs an access operation to the additional reagent storage portion 111 upon receiving a predetermined instruction.

19 Claims, 18 Drawing Sheets

(51) Int. Cl.
*G01N 33/493* (2006.01)
*G01N 35/04* (2006.01)
*G01N 35/00* (2006.01)

(56) References Cited

U.S. PATENT DOCUMENTS

| | | | |
|---|---|---|---|
| 5,434,083 A | 7/1995 | Mitsumaki et al. | |
| 5,897,837 A * | 4/1999 | Mizuno | G01N 35/109 422/65 |
| 6,190,617 B1 * | 2/2001 | Clark | G01N 21/03 422/562 |
| 2002/0132356 A1 * | 9/2002 | Qureshi | G01N 35/0092 422/63 |
| 2005/0123445 A1 * | 6/2005 | Blecka | G01N 35/0099 422/64 |
| 2006/0239860 A1 | 10/2006 | Evers et al. | |
| 2006/0263248 A1 | 11/2006 | Gomm et al. | |
| 2008/0014118 A1 | 1/2008 | Kitagawa et al. | |
| 2008/0311678 A1 * | 12/2008 | Ootani | G01N 35/10 436/526 |
| 2008/0318323 A1 | 12/2008 | Shintani et al. | |
| 2009/0117004 A1 * | 5/2009 | Fritchie | B03C 1/284 422/63 |
| 2010/0001854 A1 | 1/2010 | Kojima | |
| 2012/0020838 A1 | 1/2012 | Mimura et al. | |
| 2012/0039748 A1 | 2/2012 | Mimura et al. | |
| 2012/0140894 A1 | 6/2012 | Feuerlein et al. | |
| 2012/0301359 A1 | 11/2012 | Kraemer et al. | |
| 2013/0017535 A1 * | 1/2013 | Frey | G01N 35/0099 422/65 |
| 2017/0082646 A1 | 3/2017 | Wang et al. | |
| 2019/0361041 A1 | 11/2019 | Sasaki et al. | |
| 2020/0241029 A1 | 7/2020 | Imai et al. | |

FOREIGN PATENT DOCUMENTS

| | | | |
|---|---|---|---|
| JP | S63-229371 | A | 9/1988 |
| JP | H03-048161 | A | 3/1991 |
| JP | H06-018532 | A | 1/1994 |
| JP | H06-082460 | A | 3/1994 |
| JP | H06207944 | A | 7/1994 |
| JP | 2705471 | B2 | 1/1998 |
| JP | 2006250958 | A | 9/2006 |
| JP | 2008032688 | A | 2/2008 |
| JP | 2008216173 | A | 9/2008 |
| JP | 2008224384 | A | 9/2008 |
| JP | 2010-217057 | A | 9/2010 |
| JP | 2012132925 | A | 7/2012 |
| JP | 2012189611 | A | 10/2012 |
| JP | 2013-068442 | A | 4/2013 |
| JP | 2013152240 | A | 8/2013 |
| JP | 5286120 | B2 | 9/2013 |
| JP | 2013174536 | A | 9/2013 |
| JP | 2016161295 | A | 9/2016 |
| JP | 2016176777 | A | 10/2016 |
| JP | 2018-054292 | A | 4/2018 |
| JP | 2019-002771 | A | 1/2019 |
| WO | 2006107016 | A1 | 10/2006 |
| WO | 2010117044 | A1 | 10/2010 |
| WO | 2015183800 | A1 | 12/2015 |
| WO | 2018155049 | A1 | 8/2018 |
| WO | 2019053991 | A1 | 3/2019 |

OTHER PUBLICATIONS

Search Report dated Dec. 23, 2022 in European Application No. 20796400.8.
International Preliminary Report on Patentability dated Jul. 9, 2021 in International Application No. PCT/JP2020/004289.
Written Opinion dated Mar. 19, 2020 in International Application No. PCT/JP2020/004289.
Search Report dated Mar. 19, 2020 in International Application No. PCT/JP2020/004289.

* cited by examiner

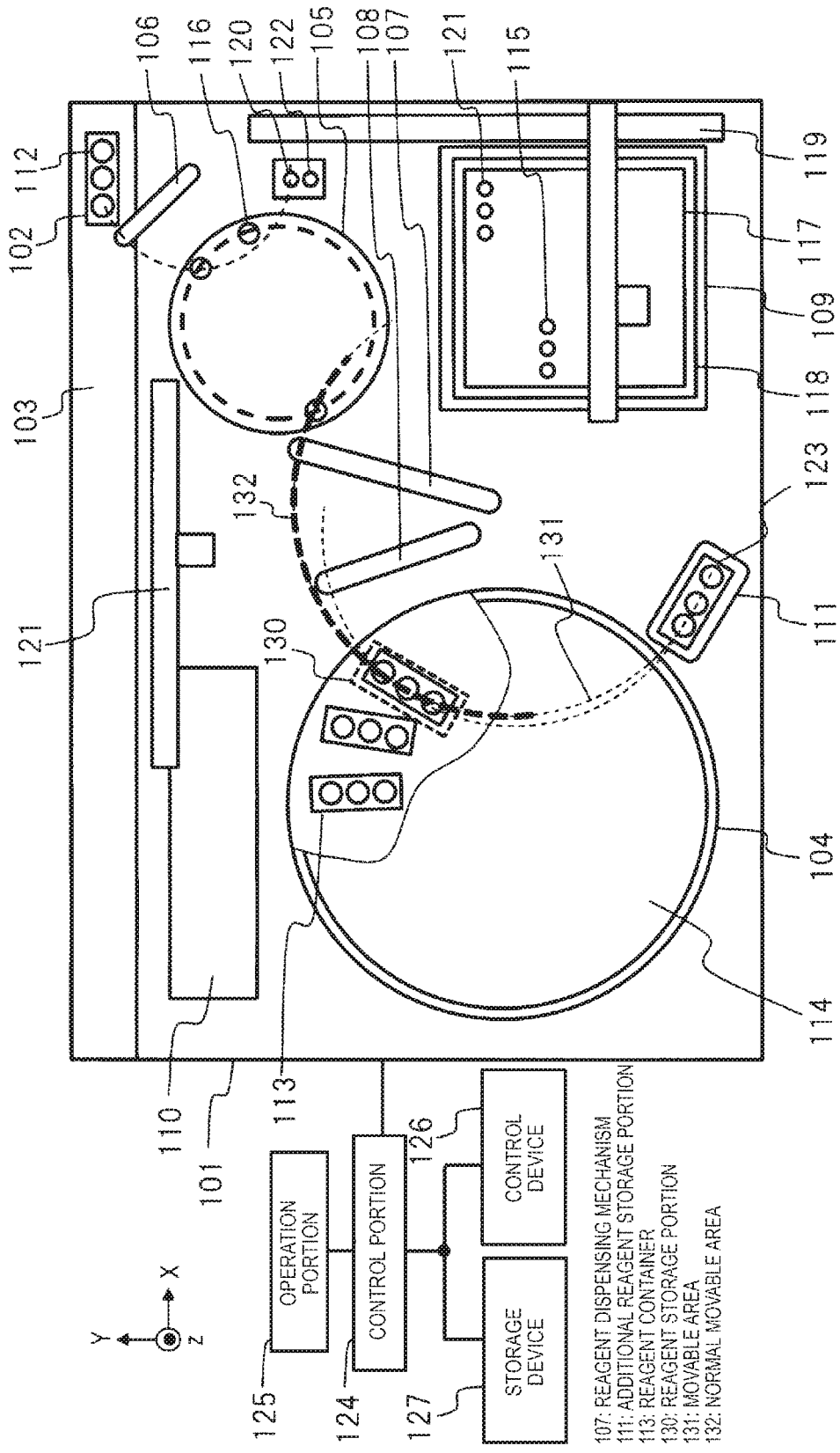

[Fig. 2]
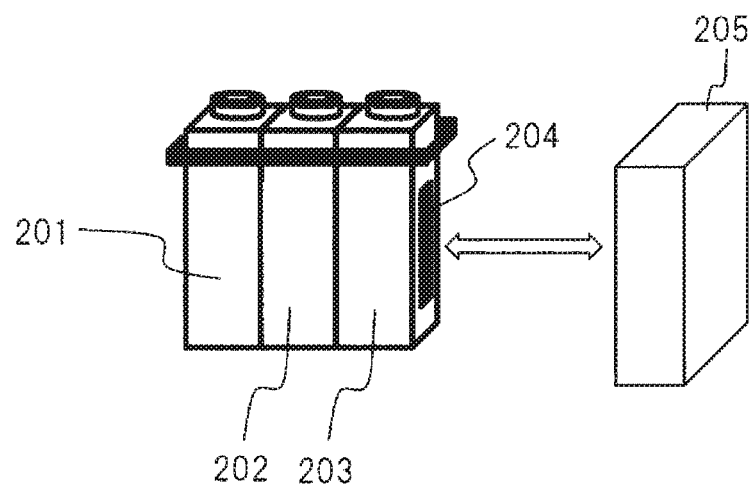

[Fig. 3A]
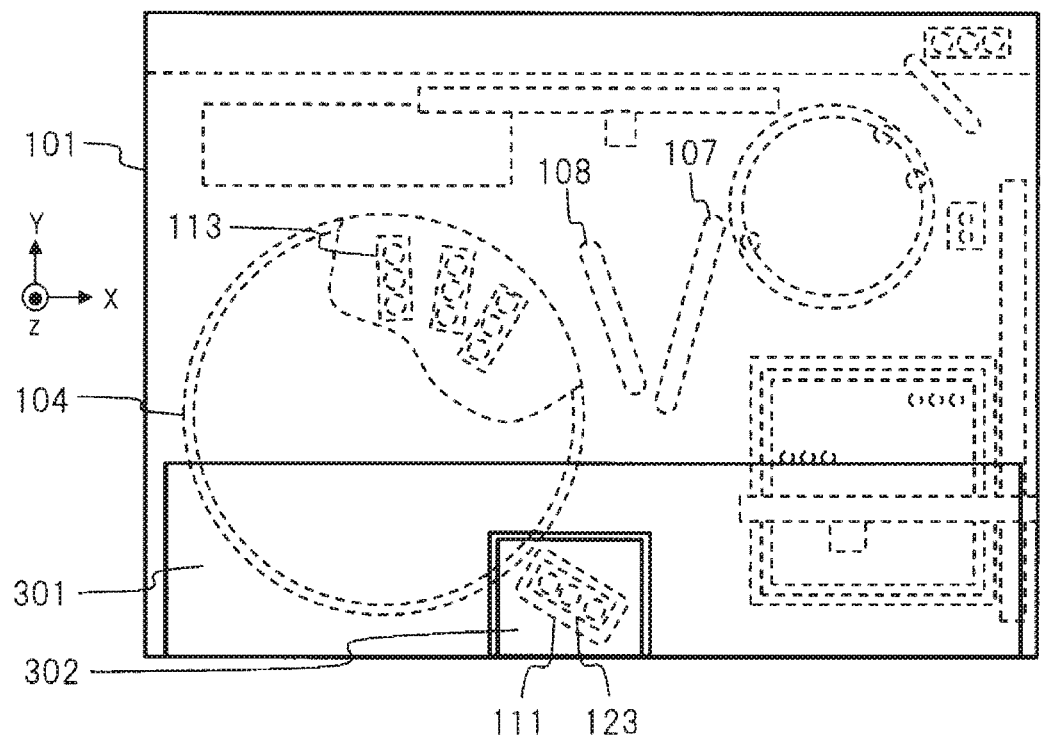
[Fig. 3B]
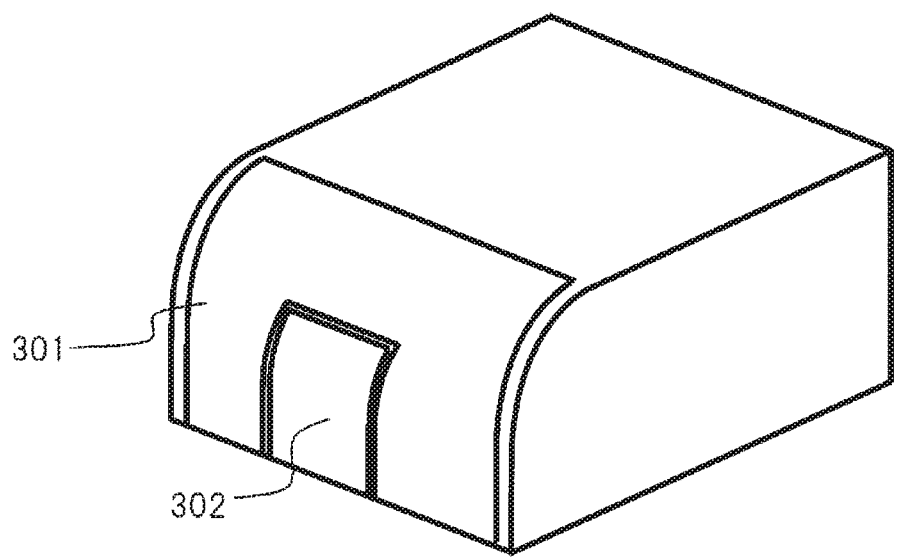

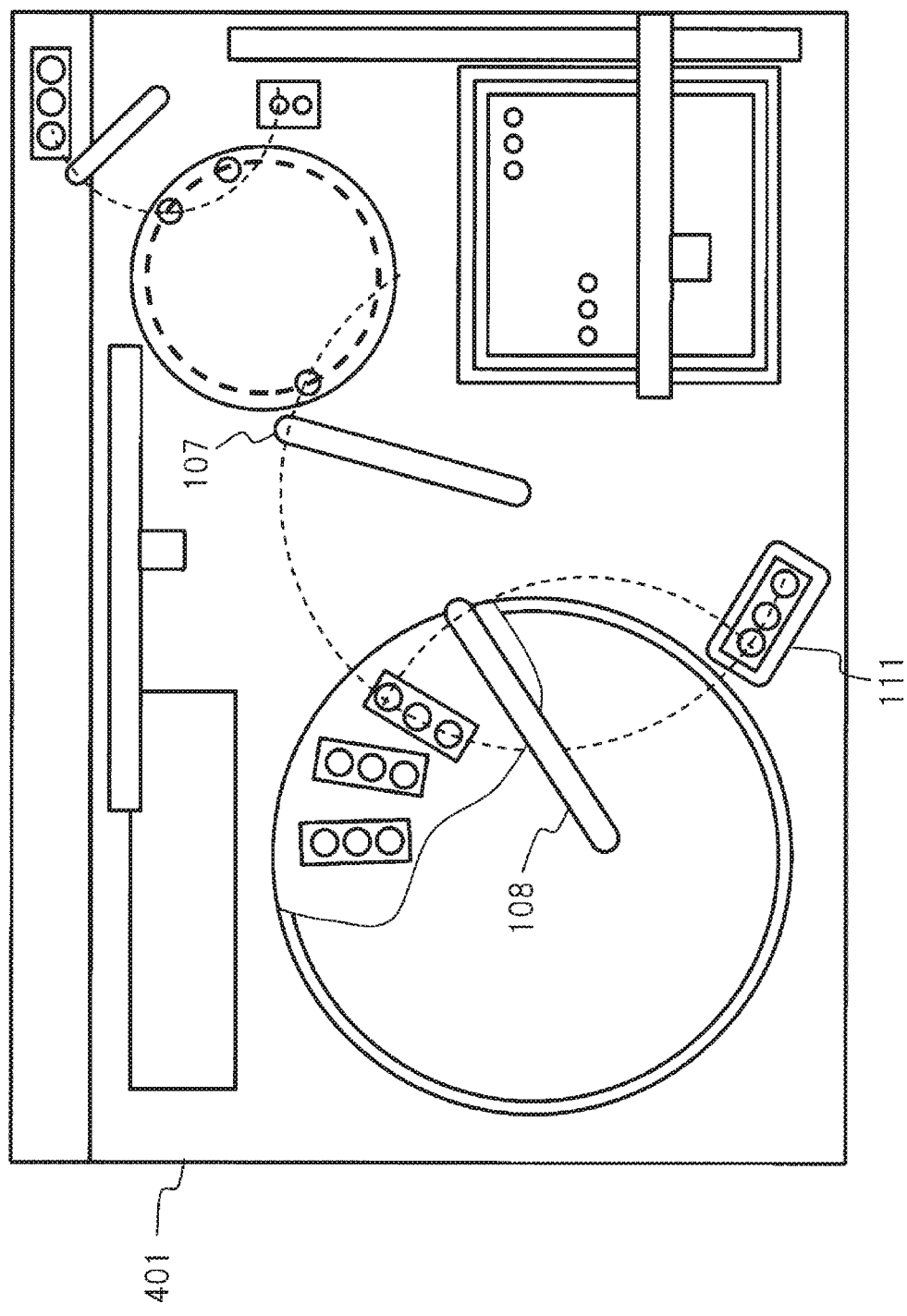
[Fig. 4]

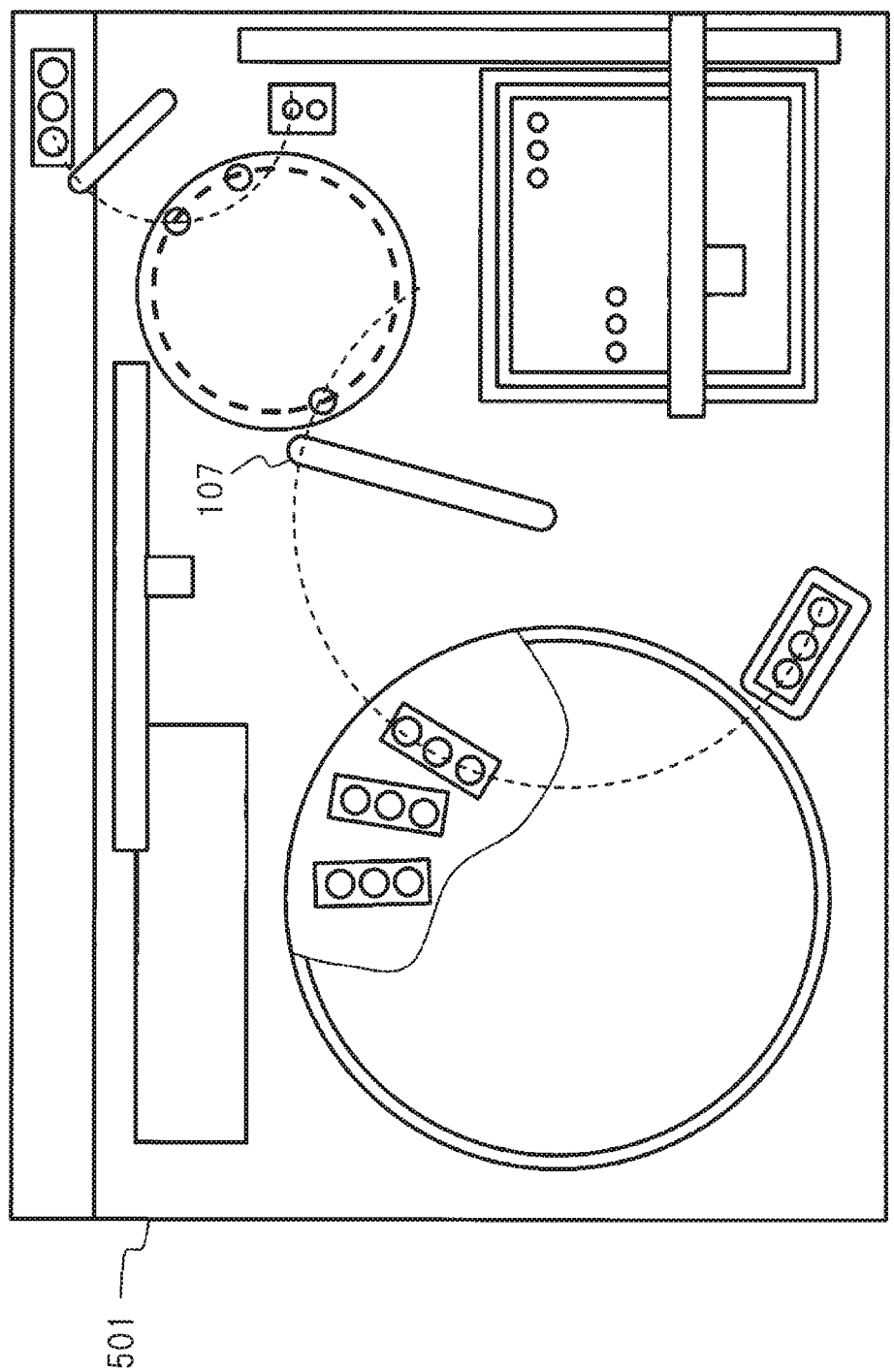

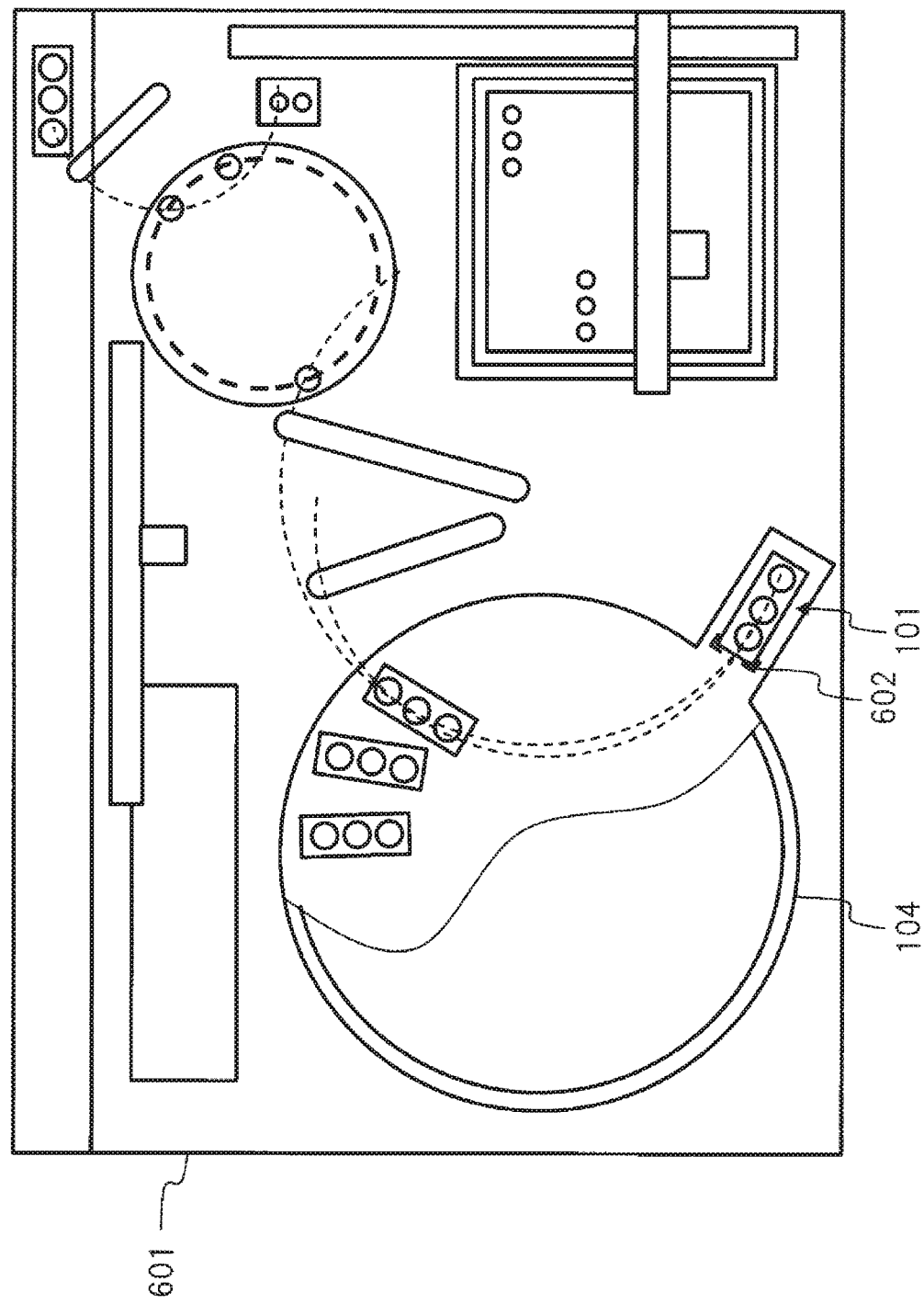
[Fig. 6]

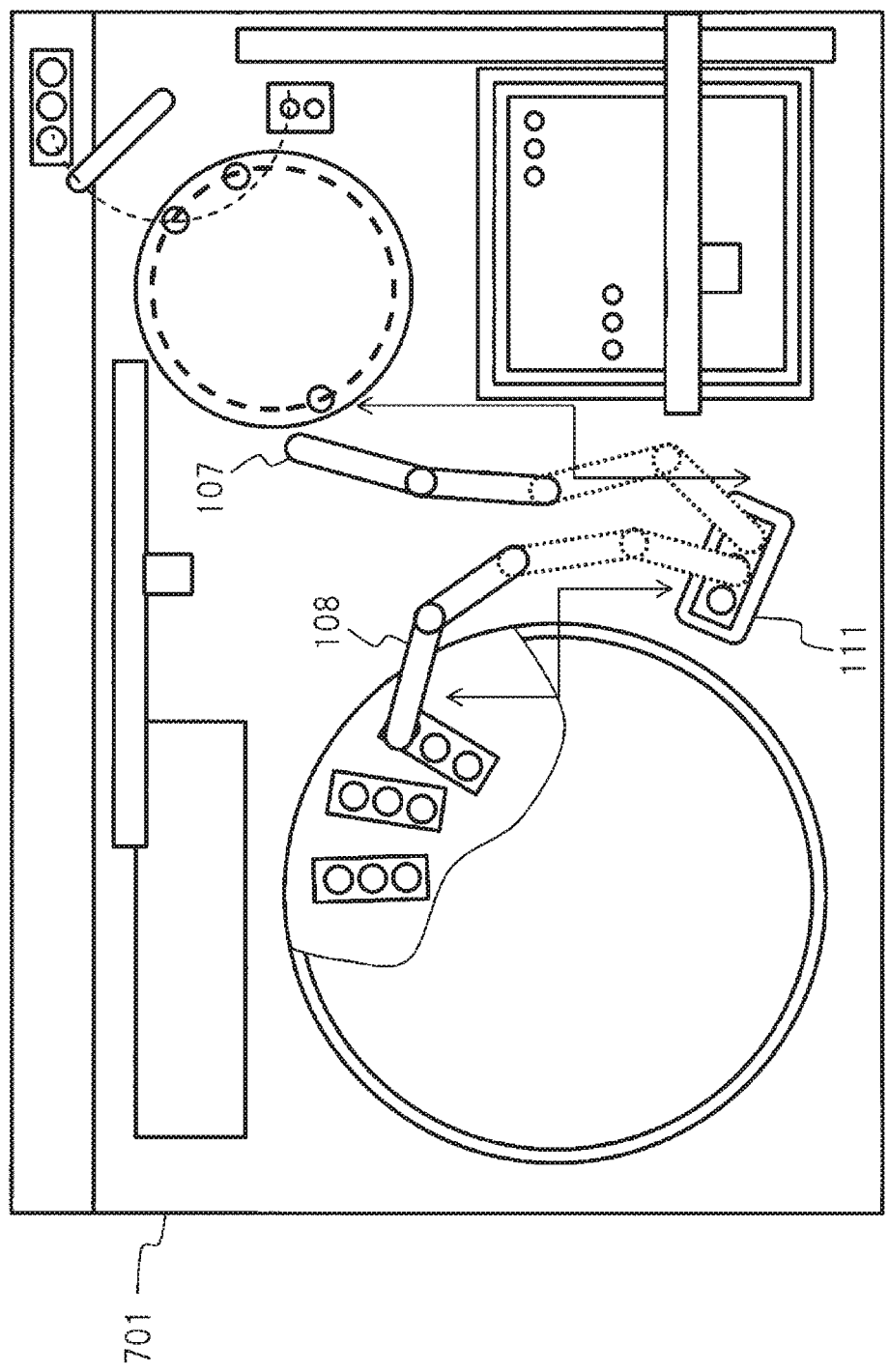

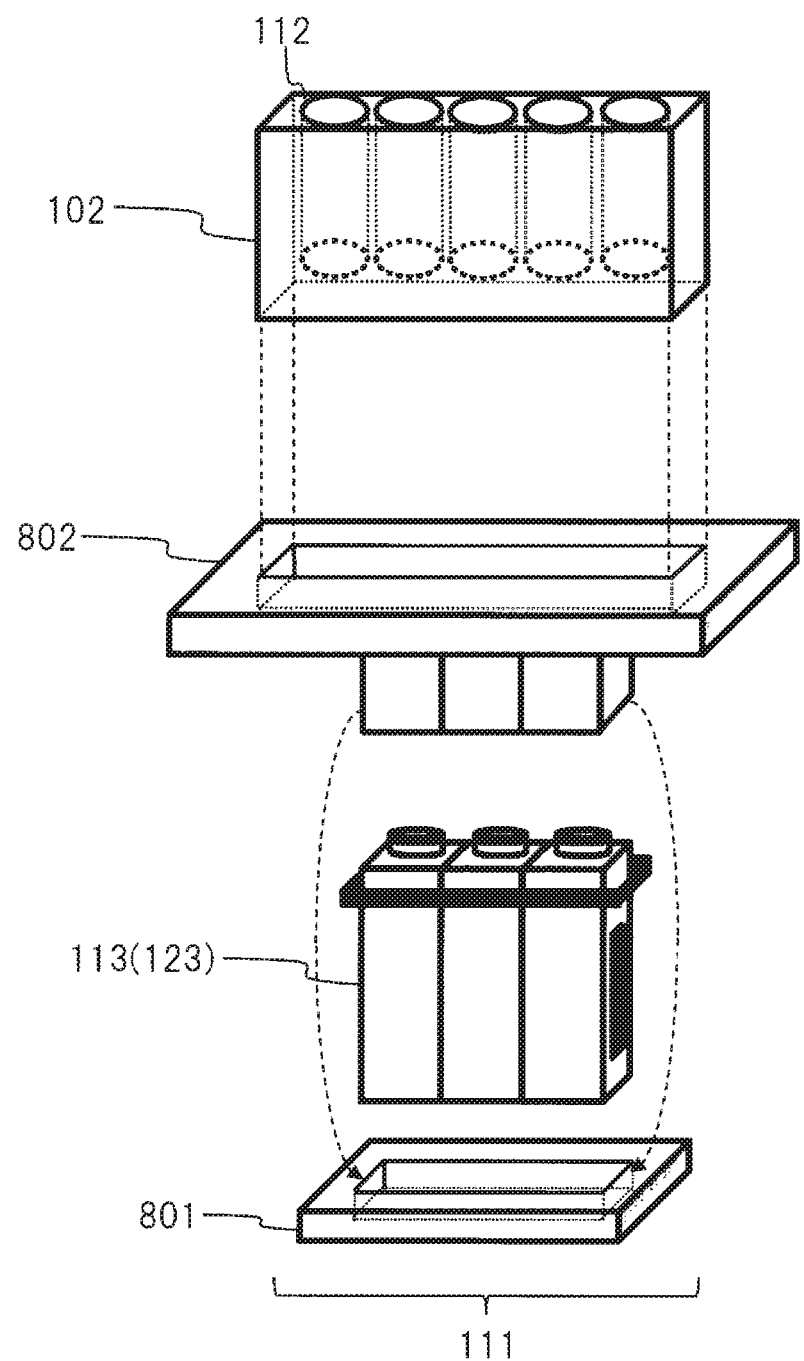
[Fig. 8]

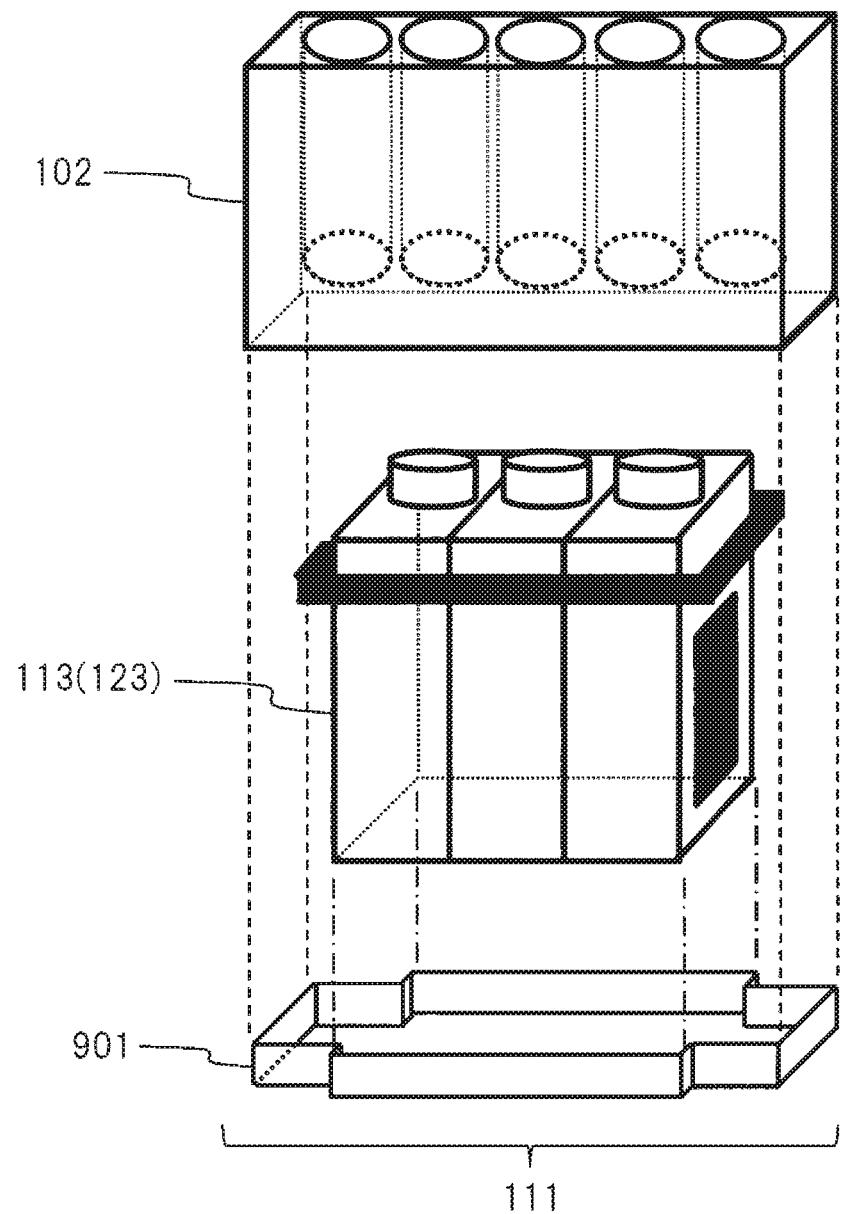
[Fig. 9]

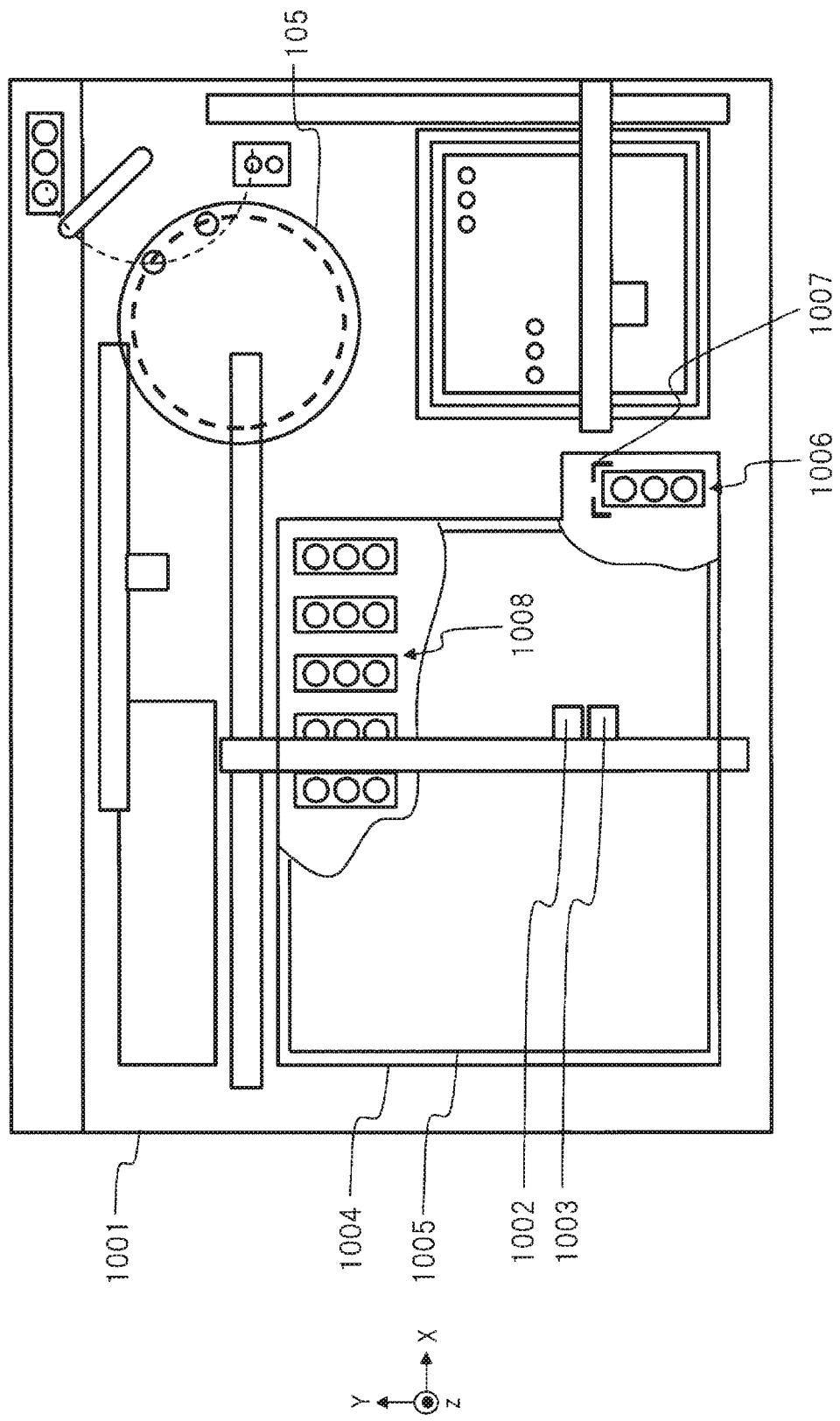
[Fig. 10]

[Fig. 11A]
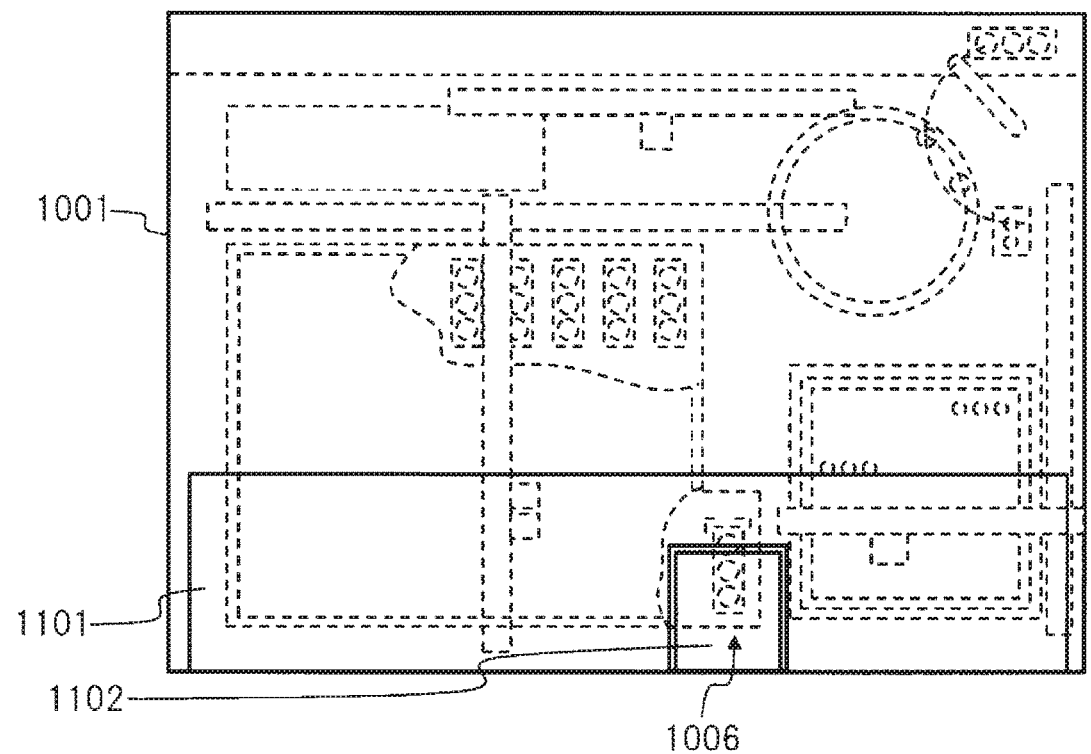
[Fig. 11B]
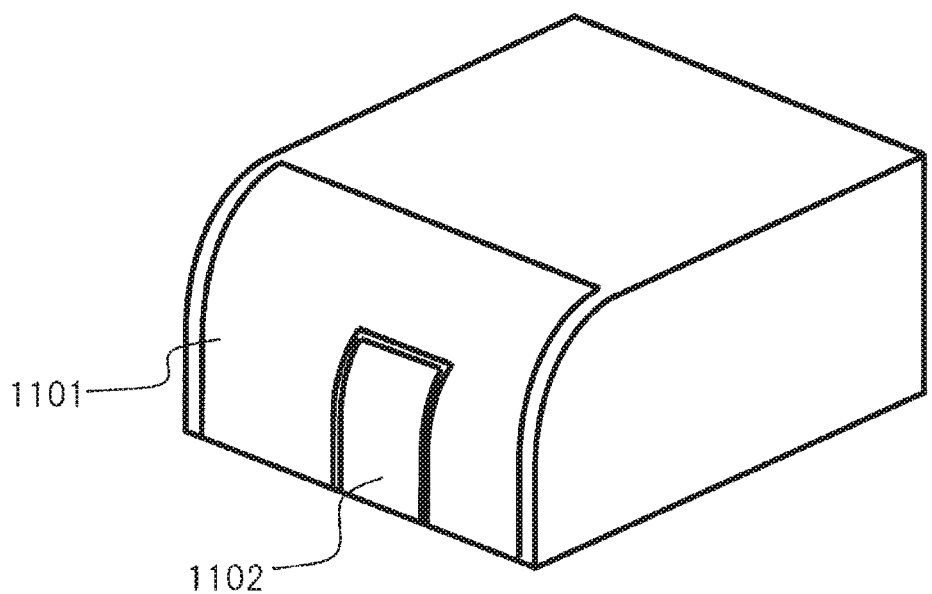

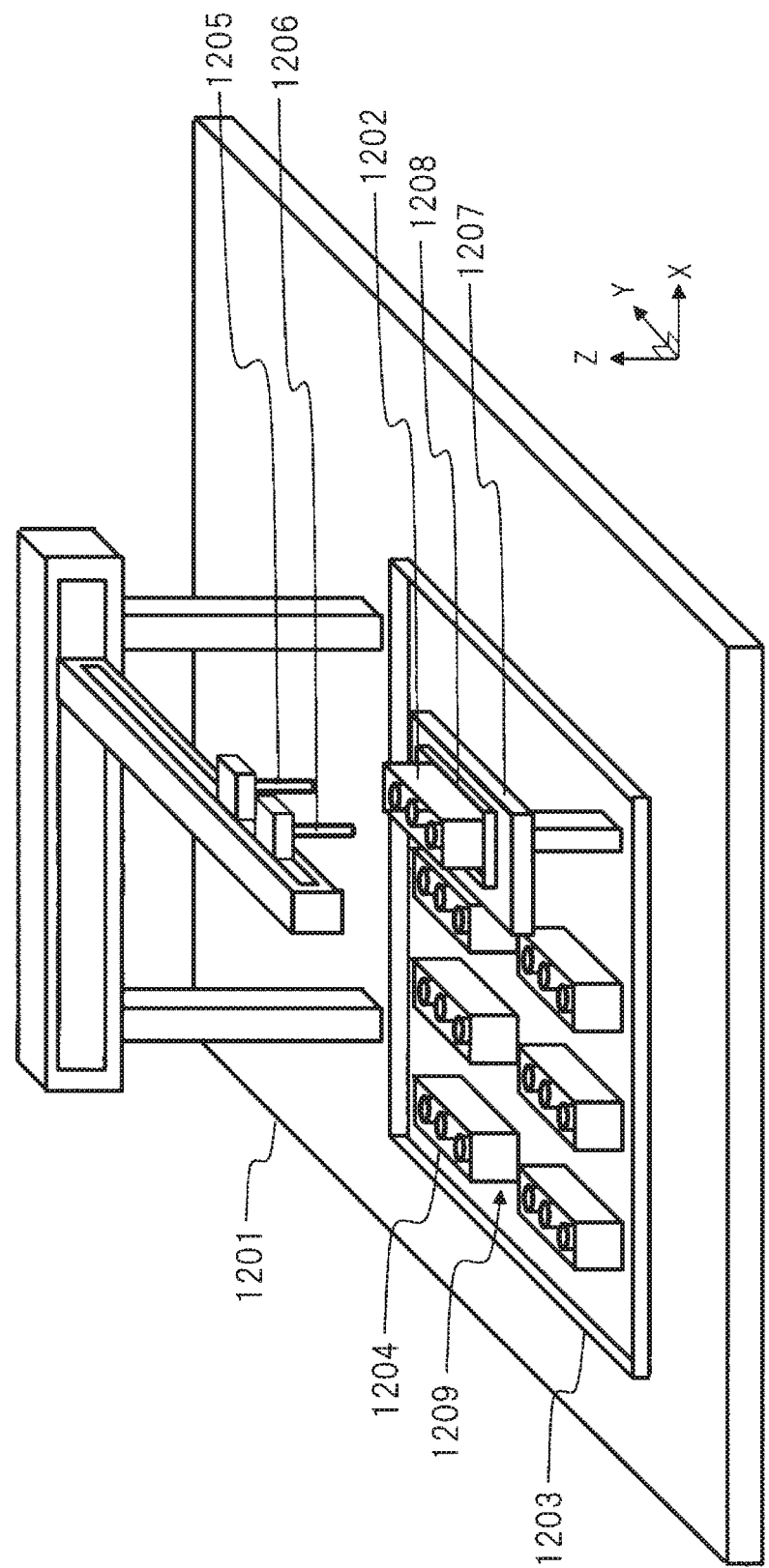
[Fig. 12]

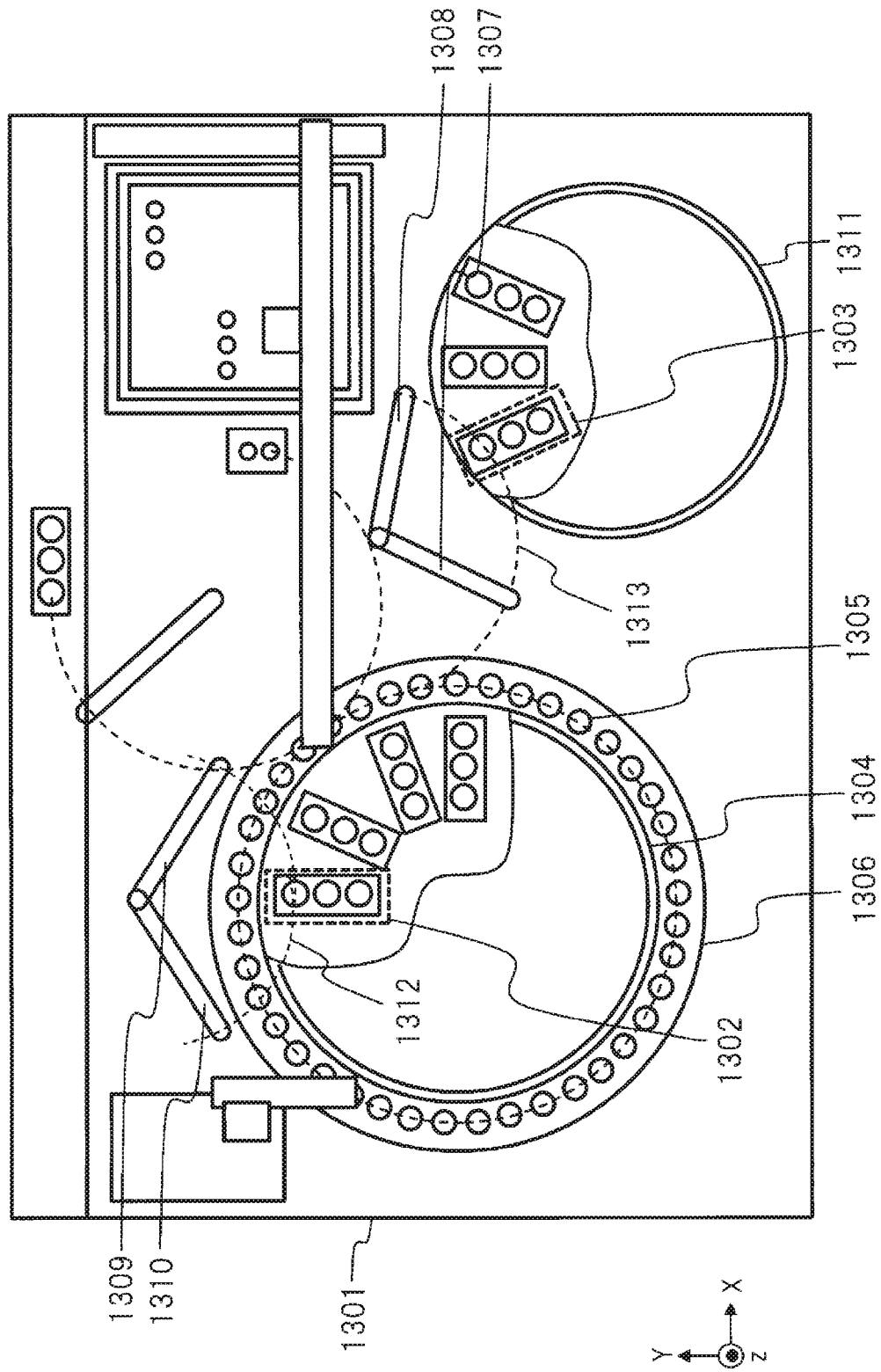
[Fig. 13]

[Fig. 14A]
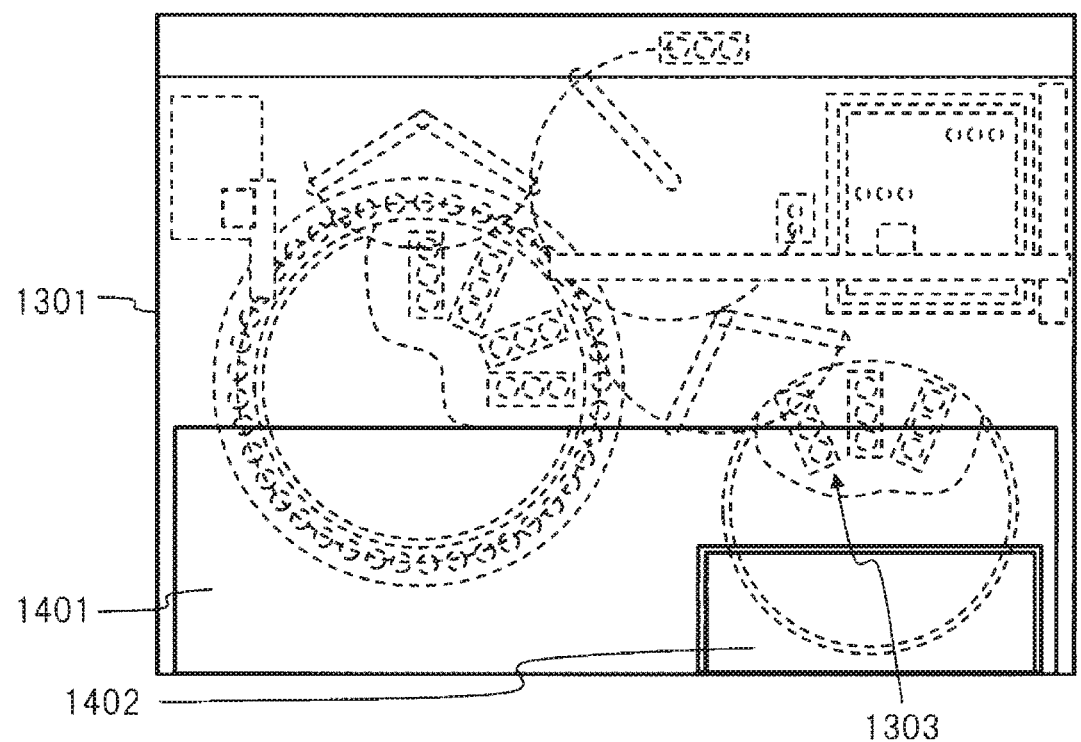
[Fig. 14B]
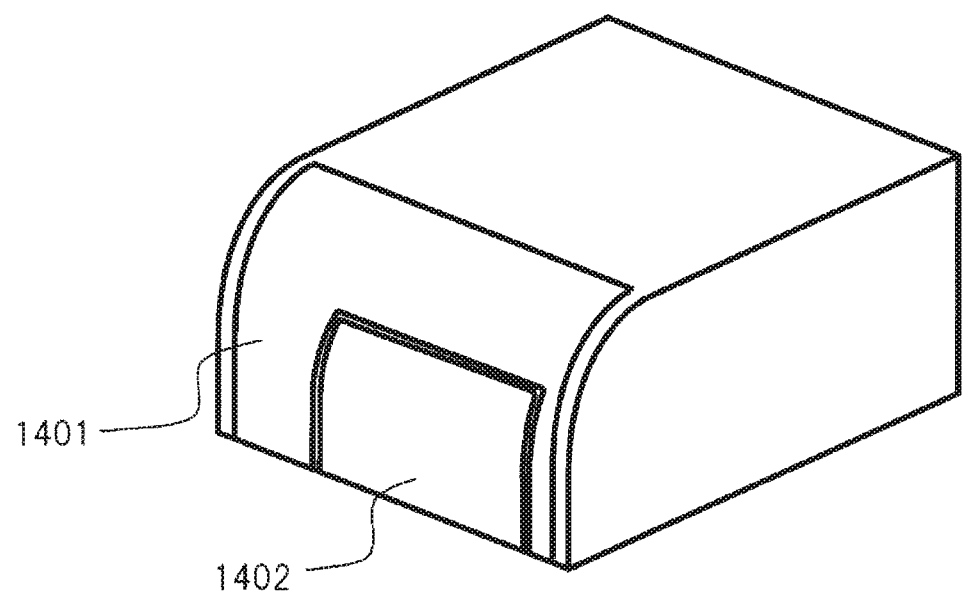

[Fig. 15A]
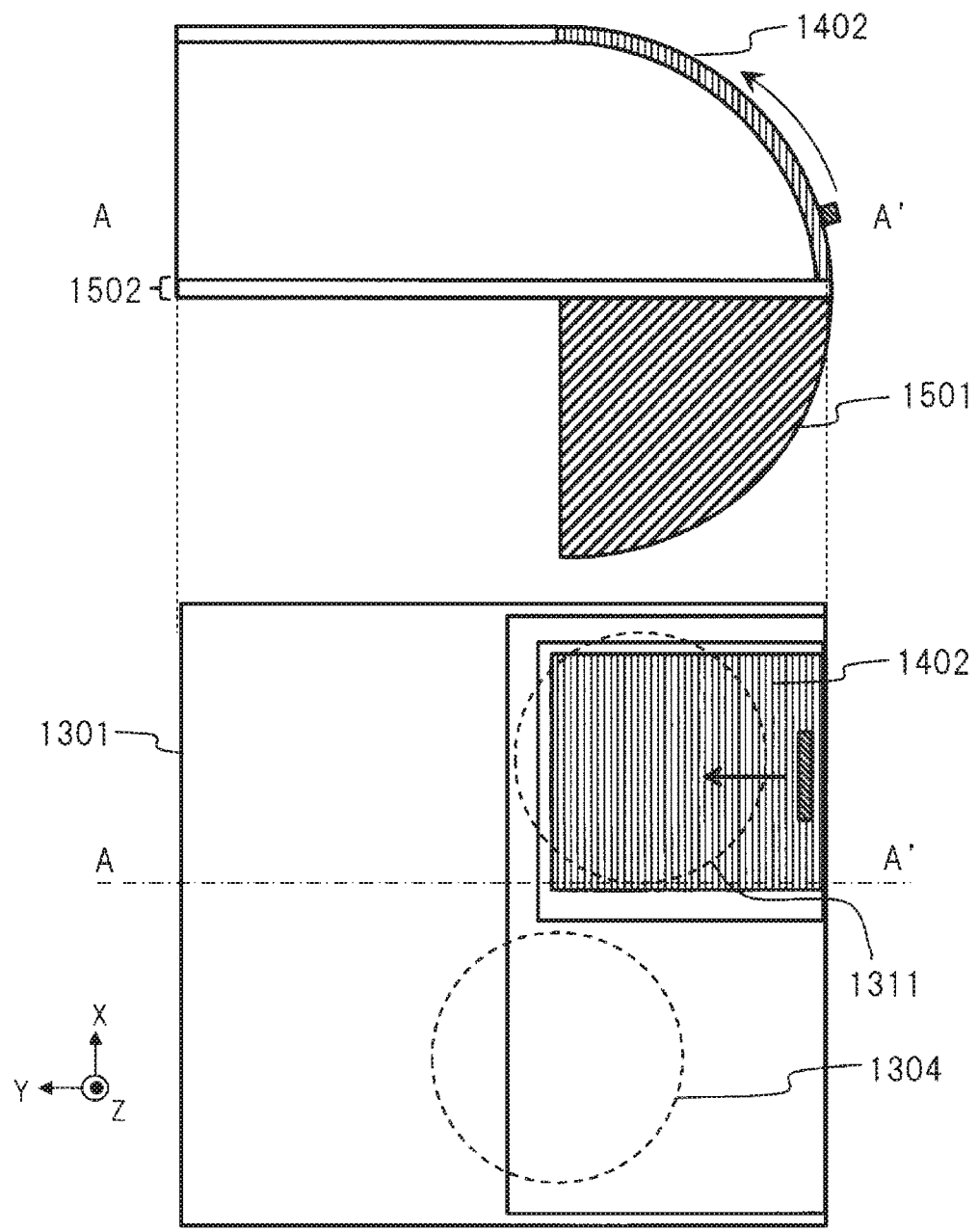

[Fig. 15B]
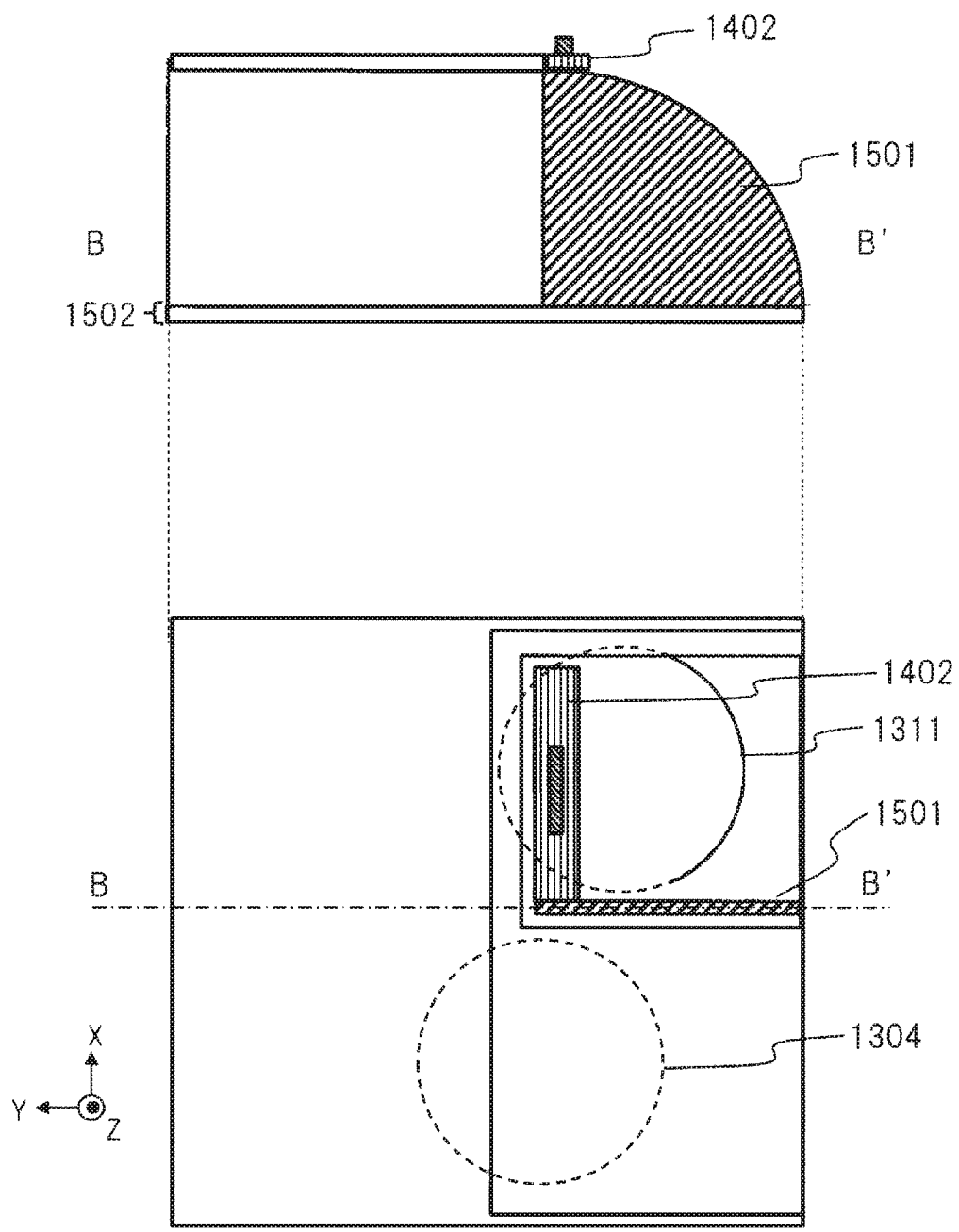

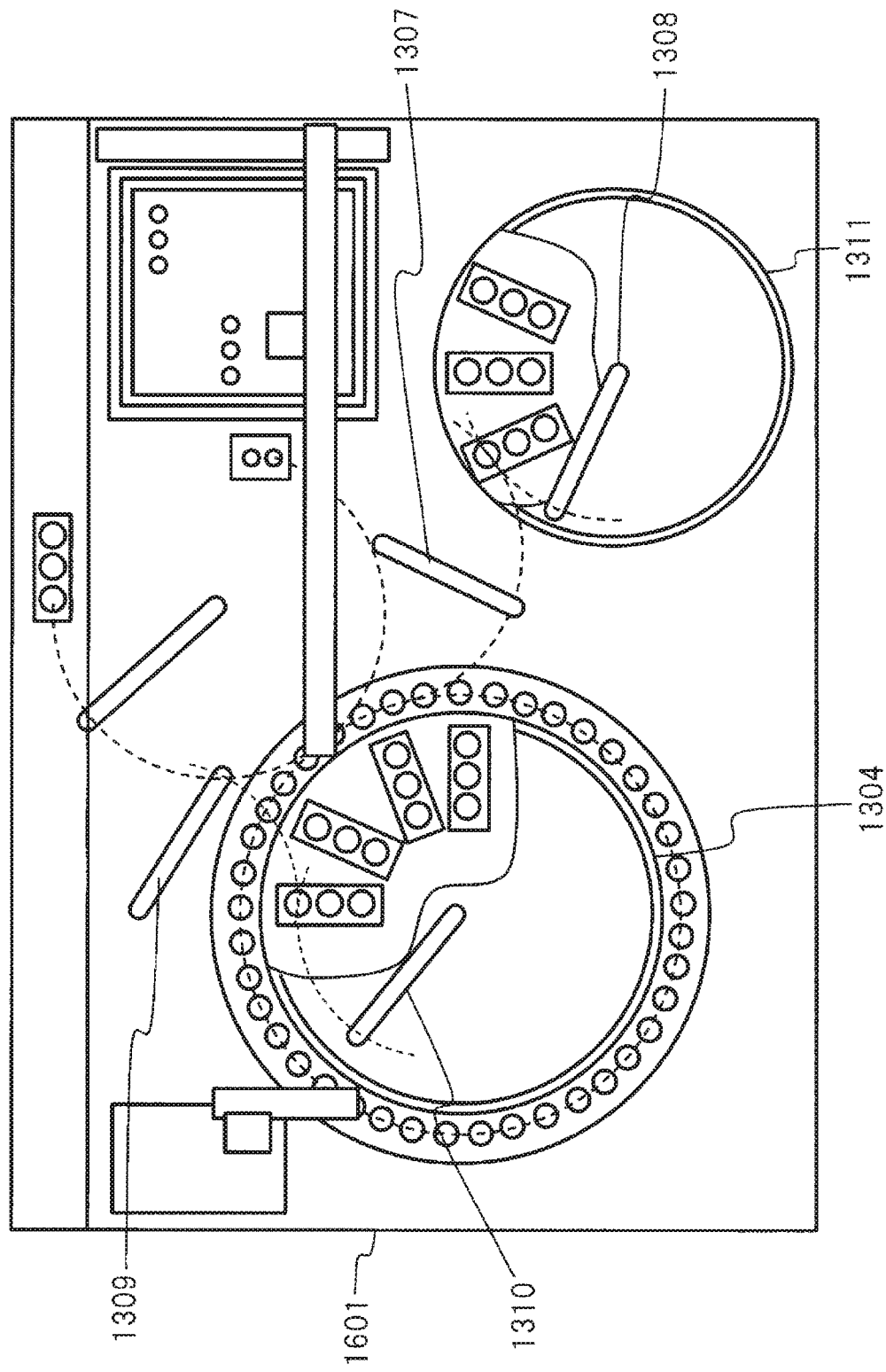
[Fig. 16]

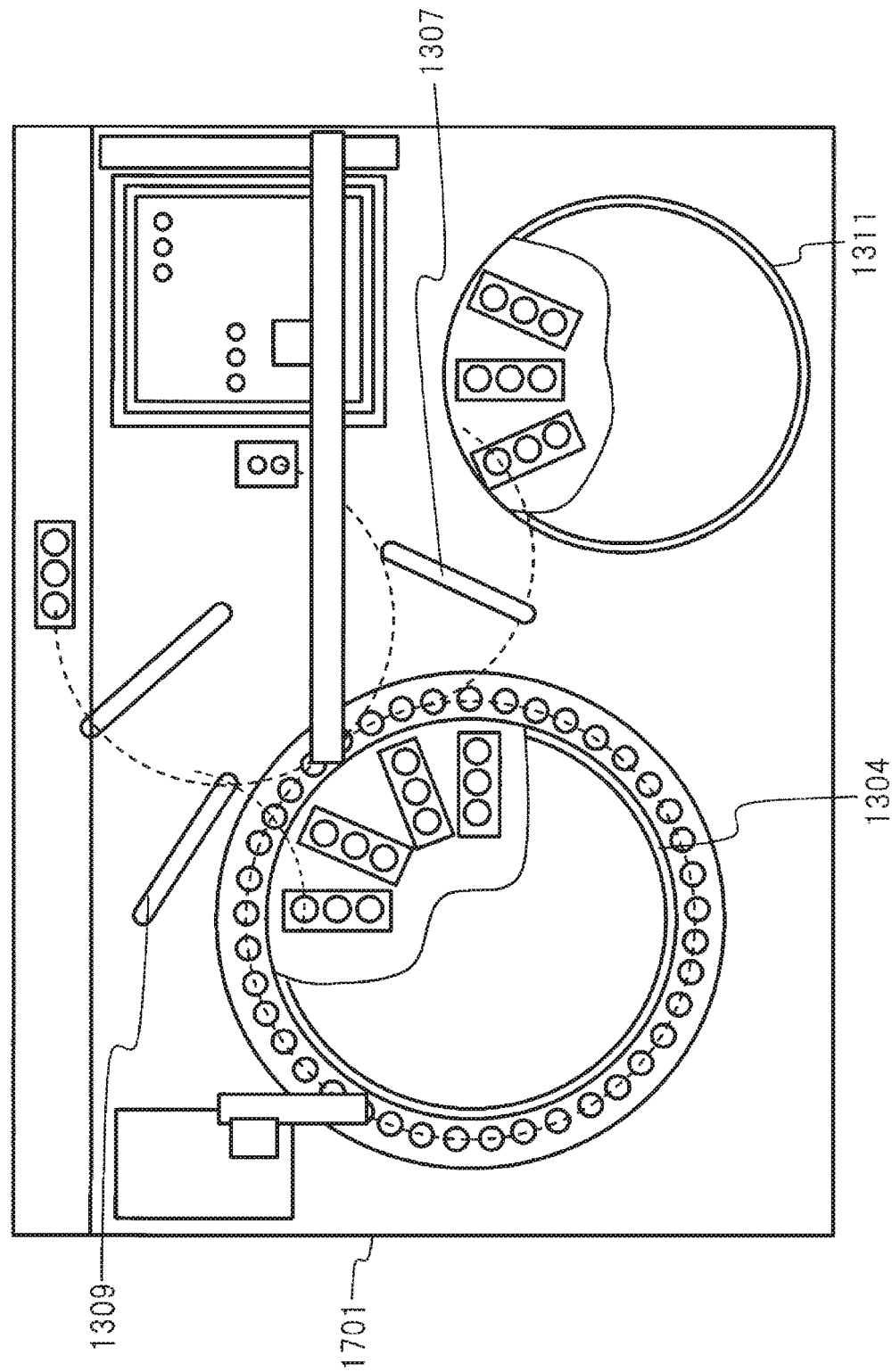
[Fig. 17]

AUTOMATIC ANALYSIS DEVICE

TECHNICAL FIELD

The present invention relates to an automatic analysis device.

BACKGROUND ART

In an automatic analysis device such as a biochemical analysis device and an immunoanalysis device, in order to perform analysis on specific components contained in specimens such as serum and urine, following three processes are generally performed automatically on the automatic analysis device. In a first process, an analytical sample collected from the specimen such as serum or urine and a reagent that specifically combines with a component to be analyzed in the sample are mixed in a reaction container on the device to react with each other. In a second process, after reacting for a certain period of time, an amount of the reagent combined with the sample is converted into a detectable signal amount by using characteristics of the reagent. For example, when a reagent whose color changes by reacting with a sample is used, an amount of the reagent combined with the sample can be converted into a signal amount by measuring absorbance. In a third process, the obtained signal amount is converted into a concentration of the component to be analyzed in the sample by using a relationship between the concentration and the signal amount, which is previously obtained by analyzing a sample of known concentration.

The automatic analysis device is generally required to simultaneously analyze a plurality of components (items) for a plurality of specimens. For example, when the immunoanalysis device is used for screening for hepatitis cancer testing, analysis of a plurality of items, such as hepatitis A, hepatitis B and hepatitis C, is automatically performed in parallel on a plurality of serum specimens, so that physicians can perform diagnosis and treatment as early as possible. In order to implement such an automatic analysis of a plurality of items, the automatic analysis device generally includes a reaction portion capable of holding a plurality of reaction containers, and a reagent storage portion capable of holding reagent containers of the plurality of items. When the plurality of items are analyzed, appropriate reagents are dispensed from the reagent container to the reaction container respectively according to a plurality of analysis items, so that the analysis of the plurality of items can be performed efficiently.

For example, an automatic analysis device illustrated in PTL 1 is one example of the above-mentioned automatic analysis device for analyzing a plurality of items. The automatic analysis device of PTL 1 includes a reagent disk for holding a plurality of reagent containers, a reaction portion holding a plurality of reaction containers, and a reagent dispensing probe for dispensing a reagent from a reagent container to a reaction container. When the plurality of items are analyzed, appropriate reagents are respectively dispensed from the reagent containers to the reaction containers respectively by adjusting rotation of the reagent disk and movement of the reagent dispensing probe according to the plurality of analysis items.

Further, PTL 2 discloses an automatic analysis device including a reagent container transfer mechanism for transferring a reagent between an inside of the reagent disk and an outside of the reagent disk on the reagent disk. PTL 3 discloses an automatic analysis device including a reagent container introducing portion on a front portion of the automatic analysis device.

CITATION LIST

Patent Literature

PTL 1: JP-A-2016-161295
PTL 2: JP-A-2012-189611
PTL 3: JP-A-2012-132925

SUMMARY OF INVENTION

Technical Problem

For example, applications such as simple diagnosis and rapid diagnosis require relatively small and inexpensive automatic analysis devices. In particular, in such an automatic analysis device, it is not easy to replace the reagent container during an operation of the device. In other words, during the operation of the analysis device, the reagent disk and the reagent dispensing probe move intricately according to the analysis items. Therefore, it is difficult for an operator to directly access the reagent disk device and to replace the reagent container during the operation of the analysis device.

When a supplement and a replacement of a reagent is necessary during the operation of the analysis device, the operator must either wait for the analysis device to finish operating and turn into a standby state, or suspend the analysis and set the device to the standby state. However, in this case, during the analysis device transiting between the standby state and the analysis operation, a certain preparation time may be required for a reset operation and a cleaning operation of the mechanism. In addition, when the analysis is interrupted, it may be necessary to perform the analysis again from beginning on the sample being analyzed on the device.

Therefore, it is conceivable to use the automatic analysis device of PTL 2 or PTL 3. The automatic analysis device of PTL 2 includes the reagent container transfer mechanism for transferring the reagent between the inside of the reagent disk and the outside of the reagent disk. Movable portions such as the reagent dispensing probes do not directly access a provided position of the reagent container in the reagent container transfer mechanism. Therefore, even when the analysis device is in operation, the operator can provide an additional reagent container in the provided position of the reagent container of the reagent container transfer mechanism. The reagent container transfer mechanism determines a timing at which the additional reagent container can be transferred inside the reagent disk according to an operation schedule of the reagent disk, and automatically performs a taking-in operation of the reagent container on the reagent disk. Conversely, even when the reagent container is taken out of the reagent disk, the reagent container transfer mechanism determines a transferable timing and automatically performs a taking-out operation.

In addition, the automatic analysis device of PTL 3 includes a reagent container introducing portion on the front portion. Movable portions such as a reagent dispensing probe do not directly access the reagent container introducing portion. Therefore, similarly to a configuration of PTL 2, the operator can provide the reagent container even during the operation of the analysis device. In addition, the reagent container transfer mechanism can implement the taking-in operation or the taking-out operation of the reagent container on the reagent disk in the transferable timing.

Thus, when the configurations of PTL 2 and PTL 3 are used, it is possible to replace the reagent container even during the operation of the analysis device. However, both of these configurations require a reagent container transfer mechanism for transferring the reagent containers. Since the reagent container transfer mechanism usually includes a motor, a transfer path, a control portion for transfer, and the like, an increase in a size of the device and an increase in device cost are caused. For this reason, it is not easy to mount such a mechanism especially on the small-scale automatic analysis device.

The invention has been made in view of such circumstances, and one of objects thereof is to provide an automatic analysis device that can easily realize introduction and replacement of additional reagents in operation even in a small-scale configuration.

The object described above, other objects, and novel features of the invention will be clarified with the description of this specification and the accompanying drawings.

Solution to Problem

An outline of a representative embodiment among the embodiments disclosed in the invention will be briefly described as follows.

An automatic analysis device according to an embodiment includes a dispensing mechanism that dispenses a reagent from a reagent container in which the reagent is stored, a first and a second storage area that store the reagent container. The first storage area is located in a normal movable area which is a part of a movable area of the dispensing mechanism, and the second storage area is located in an area other than the normal movable area in the movable area of the dispensing mechanism. The dispensing mechanism performs an access operation in the normal movable area when a normal operation is performed, and performs the access operation on the second storage area when a predetermined instruction is received.

Advantageous Effect

To briefly describe the effects obtained according to the representative embodiments of the inventions disclosed in the present application, easily introduction and replacement of an additional reagent during the operation even in a small-scale automatic analysis device can be performed.

BRIEF DESCRIPTION OF DRAWINGS

FIG. 1 is a schematic view illustrating a configuration example of an automatic analysis device according to Embodiment 1.

FIG. 2 is a schematic view illustrating a configuration example of a reagent container in FIG. 1.

FIG. 3A is a plan view illustrating a configuration example of a cover mounted on the automatic analysis device in FIG. 1.

FIG. 3B is a perspective view of FIG. 3A.

FIG. 4 is a schematic view illustrating a configuration example obtained by modifying the automatic analysis device in FIG. 1.

FIG. 5 is a schematic view illustrating a configuration example obtained by modifying the automatic analysis device in FIG. 1.

FIG. 6 is a schematic view illustrating a configuration example obtained by modifying the automatic analysis device in FIG. 1.

FIG. 7 is a schematic view illustrating a configuration example obtained by modifying the automatic analysis device in FIG. 1.

FIG. 8 is a view illustrating an example of a method of using an additional reagent storage portion in the automatic analysis device according to Embodiment 2.

FIG. 9 is a view illustrating another example of a method of using the additional reagent storage portion in the automatic analysis device according to Embodiment 2.

FIG. 10 is a schematic view illustrating a configuration example of an automatic analysis device according to Embodiment 3.

FIG. 11A is a plan view illustrating a configuration example of a cover mounted on the automatic analysis device in FIG. 10.

FIG. 11B is a perspective view of FIG. 11A.

FIG. 12 is a schematic view illustrating a configuration example of an automatic analysis device according to Embodiment 4.

FIG. 13 is a schematic view illustrating a configuration example of an automatic analysis device according to Embodiment 5.

FIG. 14A is a plan view illustrating a configuration example of a cover mounted on the automatic analysis device in FIG. 13.

FIG. 14B is a perspective view of FIG. 14A.

FIG. 15A is a schematic view illustrating a configuration example of a guard member.

FIG. 15B is a schematic view illustrating a configuration example of the guard member.

FIG. 16 is a schematic view illustrating a configuration example obtained by modifying the automatic analysis device in FIG. 13.

FIG. 17 is a schematic view illustrating a configuration example obtained by modifying the automatic analysis device in FIG. 13.

DESCRIPTION OF EMBODIMENTS

In the following embodiments, description may be divided into a plurality of sections or embodiments if necessary for convenience, unless particularly specified, these embodiments are not independent with each other, but in a relationship in which one embodiment is a variation, detailed description, supplementary description, or the like of a part or all of another embodiment. In one embodiment, when a number and the like (including number of article, numeric value, quantity, range and the like) of an element is referred to, these parameters are not limited to the specific numbers, and the values may be greater or less than these specific numbers, unless otherwise specified or unless the specific numbers are clearly limited to specific numbers in principle.

Further, in the following embodiments, it is needless to say that the constituent elements (including element steps and the like) are not necessarily essential, unless particularly specified or considered to be apparently essential in principle. Similarly, in the following embodiments, when a reference is made to a shape of the components, a positional relationship thereof, and the like, substantially approximate and similar shapes and the like are included therein unless otherwise specified or except a case where it can be thought that they are apparently excluded in principle.

Hereinafter, embodiments of the invention will be described in detail with reference to the drawings. In all the drawings for describing the embodiments, the same members are denoted by the same reference numerals in principle, and the repetitive description thereof will be omitted.

Embodiment 1

<Overall Schematic Configuration and General Operation of Automatic Analysis Device>

FIG. 1 is a schematic view illustrating a configuration example of an automatic analysis device according to Embodiment 1. Here, an immunoanalysis device that uses an antigen as an analysis target and performs luminescence analysis using a luminescent labeling substance that specifically binds to the antigen to be analyzed is assumed as an example of the automatic analysis device. An automatic analysis device 101 in FIG. 1 includes a rack transport line 103 that transports a specimen rack (abbreviated as rack) 102, a reagent cold storage unit 104, an incubator disk (reaction disk) 105, a sample dispensing mechanism (sample dispensing mechanism) 106, a reagent dispensing mechanism 107, a reagent stirring mechanism 108, an expendable item transport unit 109 and a detection portion unit 110. In addition to these, the automatic analysis device 101 further includes an additional reagent storage portion 111. In the description, each of the above components may be called as a unit.

The rack 102 accommodates a plurality of sample containers (sample containers) 112 that stores biological samples (abbreviated as samples) such as blood and urine, and the rack 102 is transported on the rack transport line 103 in a state where the sample containers 112 are accommodated. A plurality of reagent containers (analysis reagent containers) 113 that store various reagents (analysis reagents) used for sample (also referred to as samples or specimens) analyzing are accommodated in the reagent cold storage unit 104. In addition, the reagent containers 113 in the cold storage unit 104 are kept cool by a freezing machine. At least a part of an upper surface of the reagent cold storage unit 104 is covered by a reagent disk cover 114.

The incubator disk 105 includes a reaction container disposition portion 116 in which a plurality of reaction containers 115 used for reacting the sample and a reagent are disposed, and a temperature adjustment mechanism used for adjusting a temperature of the reaction containers 115 to a desired temperature. The sample dispensing mechanism 106 has a rotary drive mechanism and an up-down drive mechanism, and dispenses the sample from the sample container 112 to the reaction container 115 accommodated in the incubator disk 105 by these drive mechanisms. Similarly, the reagent dispensing mechanism 107 also has a rotary drive mechanism and an up-down drive mechanism, and dispenses the reagent from the reagent container 113 to the reaction container 115 accommodated in the incubator disk 105 by these drive mechanisms. The same applies to drive mechanisms of the reagent stirring mechanism 108.

The detection portion unit 110 includes a photomultiplier tube, a light source lamp, a spectrometer and a photo diode, has a function of adjusting temperatures thereof, and analyzes a reaction solution. A transport mechanism 121 is a mechanism for transporting the reaction container to the detection portion unit 110, and includes rails provided in X-axis and Z-axis directions. The expendable item transport unit 109 includes an accommodation container holding portion 118 and a transport mechanism 119. An expendable item accommodation container 117 stores a plurality of expendable items used for sample analysis, such as the reaction container 115 and a dispensing tip 121. The transport mechanism 119 grips the reaction container 115 and the dispensing tip 121 on the expendable item accommodation container 117 and transports them to a predetermined position.

Specifically, the transport mechanism 119 includes rails provided in the X-axis, Y-axis, and Z-axis directions, transports the reaction container 115 accommodated in the expendable item accommodation container 117 to the incubator disk 105 via the rails, and transports the dispensing tip 121 to a chip mounting position 122 via the rails. In addition, the used reaction container 115 on the incubator disk 105 is destroyed in a disposal hole 120. Further, the transport mechanism 119 transports the unused reaction container 115 and the dispensing tip 121 which are on the expendable item accommodation container 117 respectively to the incubator disk 105 and the chip mounting position 122. Therefore, the transport mechanism 119 has an arm structure that seizes the reaction container 115 and the dispensing tip 121.

The additional reagent storage portion (additional reagent storage area) 111 stores an additional reagent container (analysis reagent container) 123 to be introduced or replaced, and can be accessed even during a normal analysis operation. That is, during the normal analysis operation, the reagent container 113 used for the analysis is stored in a normal reagent storage portion (normal reagent storage area) 130 in the reagent cold storage unit 104. The normal reagent storage portion 130 is located in a normal movable area 132 which is a part of a movable area 131 of the reagent dispensing mechanism 107. On the other hand, the additional reagent storage portion 111 is located in an area other than the normal movable area 132 in the movable area 131 of the reagent dispensing mechanism 107.

The reagent dispensing mechanism 107 performs, by rotational movement on an X-Y plane, an access operation within the normal movable area 132 during the normal analysis operation, and an access operation to the additional reagent storage portion 111 when a predetermined instruction is received. The same applies to a relationship with the reagent stirring mechanism 108, and the additional reagent storage portion 111 is located in an area other than a normal movable area in a movable area of the reagent stirring mechanism 108. Then, an additional reagent in the additional reagent container 123 is dispensed and stirred by the reagent dispensing mechanism 107 and the reagent stirring mechanism 108 when a predetermined instruction is received.

Here, for example, air can be exchanged between the normal reagent storage portion 130 and the additional reagent storage portion 111. That is, by circulating the air whose temperature is adjusted by the reagent cold storage unit 104 into the additional reagent storage portion 111, it is possible to cool the additional reagent in the additional reagent container 123, in addition to the reagent in the reagent container 113. However, in order to cool the additional reagent, the additional reagent storage portion 111 may be provided with a temperature adjustment mechanism (for example, a peltier element, or the like) different from the temperature adjustment mechanism (for example, a freezing machine or the like) of the reagent cold storage unit 104. Furthermore, the additional reagent may not be kept cool. The additional reagent storage portion 111 may store at least one or more additional reagents.

In the description, among the automatic analysis device 101, the rack transport line 103, the reagent cold storage unit 104, the incubator disk 105, the sample dispensing mechanism 106, the reagent dispensing mechanism 107, the reagent stirring mechanism 108, the expendable item transport unit 109, the detection portion unit 110, the additional reagent storage portion 111, and the like that are described above are referred to as analysis operation portions. The automatic analysis device 101 further includes, in addition to the analysis operation portions, a control portion 124 that controls overall operations of the automatic analysis device 101, and an operation portion 125.

The control portion 124 is formed of, for example, a hardware substrate, and is connected with a control device 126 such as a computer and a storage device 127 such as a hard disk. The operation portion 125 includes, for example, a display portion that is a display, and an input device such as a mouse and a keyboard. The storage device 127 stores, for example, a temperature range corresponding to each unit. The control portion 124 may be configured with a dedicated circuit substrate as a hardware, or may be configured with a software executed by a computer (for example, the control device 126) connected to the automatic analysis device 101.

When the control portion 124 is configured with the hardware, for example, a plurality of computing units that execute processing are integrated on a wiring substrate or in a semiconductor chip or in a package. When the control portion 124 is configured with the software, a high-speed general-purpose central processing unit (CPU) is mounted on the computer, and a program that executes desired computing processing is executed by the CPU. Existing devices can be upgraded by using a recording medium on which this program is recorded. In addition, these devices, circuits, and computers are connected with each other via a wired or wireless network, such that appropriate data is transmitted and received.

FIG. 2 is a schematic view illustrating a configuration example of a reagent container in FIG. 1. For example, in the immunoanalysis device that performs luminescence analysis as described above, three types of reagents, which are a labeled antibody reagent, a biotinylation antibody reagent and a streptavidin-bound magnetic particle reagent, are kitted in one reagent container 113 as a reagent kit. That is, the reagent container 113 is mainly configured with a labeled antibody reagent container 201 containing the labeled antibody reagent, a biotinylation antibody reagent container 202 containing the biotinylation antibody reagent, and a streptavidin-bound magnetic particle reagent container 203 containing the streptavidin-bound magnetic particle.

Further, a reagent label 204 indicating information of a reagent contained inside is attached to the reagent container 113. The reagent label 204 is, for example, a bar code or a radio frequency identifier (RFID), and includes information such as a target analysis item, a production lot number, a reagent kit number, an analysis possible number, a storage expiration date, an expiration date after device installation, a device installation history, a calibration validity period after calibration, and calibration data at factory shipment. The information of the reagent label 204 is read by a reading portion 205. The reading portion 205 is, for example, a bar code reader, an RFID reader writer, or the like. The reading portion 205 not only reads the reagent label 204 of the reagent container 113 stored in the reagent cold storage unit 104, but also reads a reagent label 204 of the additional reagent container 123 stored in the additional reagent storage portion 111. For this reason, depending on a reading method of the reagent label 204, the reading portion 205 is provided, for example, at two places of the reagent cold storage unit 104 and the additional reagent storage portion 111 separately.

FIG. 3A is a plan view illustrating a configuration example of a cover mounted on the automatic analysis device in FIG. 1, and FIG. 3B is a perspective view of FIG. 3A. As illustrated in FIG. 3A and FIG. 3B, the automatic analysis device 101 is mounted with a whole cover 301 and an individual cover 302. The whole cover 301 is, for example, an exit-entrance for a manual operation (introduction operation of the reagent container 113, and the like) performed on the reagent cold storage unit 104, and the individual cover 302 is an exit-entrance for a manual operation (introduction operation of the additional reagent container 123, and the like) performed on the additional reagent storage portion 111.

It is desirable that the whole cover 301 and the individual cover 302 respectively include different interlock mechanisms. For example, the interlock mechanism of the whole cover 301 prevents a manual operation performed on the automatic analysis device 101 during the analysis operation, and operates a predetermined safety function (for example, emergency stop of the device) in response to opening and closing. According to this mechanism, an operator cannot open the whole cover 301 unless the analysis operation is stopped. Meanwhile, the individual cover 302 can be opened and closed when the whole cover 301 is closed. As a result, the operator can perform the manual operation on the additional reagent storage portion 111 without stopping the analysis operation.

The reagent dispensing mechanism 107 and the reagent stirring mechanism 108 are served as one of the interlock mechanisms of the individual cover 302. For example, in a state where the individual cover 302 is opened temporarily, even when an access instruction for the additional reagent storage portion 111 is received, an access operation cannot be performed on the additional reagent storage portion 111. In addition, as another one of the interlock mechanisms of the individual cover 302, a guard member may be provided in conjunction with the opening of the individual cover 302, or as an advanced preparation before opening the individual cover 302.

The guard member includes a mechanism (for example, a shield plate that can be moved in the Z-axis direction) that can switch a state whether or not to shield the additional reagent storage portion 111 from other areas, and the access operation to the additional reagent storage portion 111 from other areas is physically prevented in a state where the additional reagent storage portion 111 is shielded. The access operation at this time is not limited to physical access operations performed by movable components such as the reagent dispensing mechanism 107 and the reagent stirring mechanism 108, but also includes other unexpected access operations. For example, scattering of harmful substances due to movement of the movable components can be mentioned.

<Method for Introducing and Replacing of Additional Reagent>

When introducing or replacing the additional reagent, the operator firstly notifies the device of a notification related to this via the operation portion 123. When the device receives the notification, the movable components such as the reagent dispensing mechanism 107 and the reagent stirring mechanism 108 are controlled so as not to access the additional reagent storage portion 111. At the same time, a lock of the individual cover 302 is released to allow free opening and closing. In this state, the operator opens the individual cover 302 and introduces (or replaces) the additional reagent container 123 into the additional reagent storage portion 111. At this time, from a viewpoint of safety, for example, it is preferable that when the individual cover 302 is opened, the above-described guard member is provided at the same time. After introducing or replacing the reagent, the operator closes the individual cover 302. When the individual cover 302 is closed, the guard member is also removed.

Next, the operator notifies the device of a notification that an introduction or a replacement of the reagent is completed via the operation portion 123. When the device receives the notification, the reading portion 205 reads the information described in the reagent label 204 of the additional reagent container 123, and registers the information in the device. Here, the notification that the introduction or the replacement of the reagent is completed is not necessarily sent. For example, instead of sending the notification, the device may be a mechanism that automatically recognizes that the individual cover 302 is closed, and operates the reading portion 205. When the information of the additional reagent is registered, the device issues a predetermined instruction to the movable components such as the reagent dispensing mechanism 107 and the reagent stirring mechanism 108. In response to this instruction, the movable components such as the reagent dispensing mechanism 107 and the reagent stirring mechanism 108 can perform the access operation to the additional reagent storage portion 111, and performs advanced preparation operations associated with the analysis such as reagent volume check of the additional reagents and pre-mixing magnetic particle reagents.

Here, information such as the device installation history (that is, whether or not the component is installed in the device) and the remaining analysis possible number described in the reagent label 204 of the additional reagent container 123 is stored in the storage device 127. For example, after an analysis requiring to use the additional reagent container 123 is performed, and when a reagent remains in the reagent container 123, the operator utilizes a pause period of the device to transfer the reagent container 123 to the reagent cold storage unit 104 by the manual operation, such that the remained reagent can be reused in the normal analysis operation. At this time, the device can take over the information of the reagent container 123 (for example, the remaining analysis possible number) by referring to the information stored in the storage device 127.

In the above description, before introducing (or replacing) the additional reagent, the operator notifies the device of a notification related thereto, so that the device performs an advanced preparation associated with the introduction (or replacement) of the additional reagent. Specifically, the advanced preparation includes releasing the lock of the individual cover 302 and limiting a movable area of the movable components such as the reagent dispensing mechanism 107 and the reagent stirring mechanism 108. However, the advanced preparation is not limited to these, and the device may perform the advanced preparation associated with the introduction (or replacement) of the additional reagent based on the information that the device has, regardless of whether or not the notification is received from the operator.

For example, the device may perform the advanced preparation associated with the introduction (or replacement) of the additional reagent in a case (A) where one of the reagents stored in the reagent cold storage unit 104 is predicted to be completely consumed, or in a case (B) where a reagent corresponding to an analysis item registered in the device is not provided in the reagent cold storage unit 104, or a case (C) where a remained amount of the reagent is dropped to a certain value or less, or the like. The case where one of the reagents is predicted to be completely consumed is, for example, a case where the remaining analysis possible number of the reagents is less than the number of analysis times instructed by the operator.

In such case, the device promotes supplement of the reagent, in addition, performs the advanced preparation associated with the introduction (or replacement) of the additional reagent by notifying the operator of the fact via the display portion such as the display. In response to this notification, the operator introduces an additional reagent to be supplied into the additional reagent storage portion 111. For example, in the cases of (A) and (C), the device recognizes the additional reagent introduced based on the reagent label 204, and in an actual stage where the reagent in the reagent cold storage unit 104 is completely consumed, the predetermined instruction is issued to the reagent dispensing mechanism 107 and the reagent stirring mechanism 108. As a result, once the reagent in the reagent cold storage unit 104 is completely consumed, the additional reagent feeding into the additional reagent storage portion 111 can be immediately performed.

Further, depending on cases, the operator can freely open the individual cover 302 and introduces the additional reagent without notifying the device in advance. Specifically, the individual cover 302 is provided with an interlock mechanism, but is not provided with the lock. When the operator opens the individual cover 302, the interlock mechanism limits the movable area of the movable components and operates the above-mentioned guard member. When the individual cover 302 is closed after the operator introduces the additional reagent, the reading portion 205 operates accordingly.

<Overall Schematic Configuration of Automatic Analysis Device (Various Modifications)>

FIGS. 4 to 7 are schematic views respectively illustrating various configuration examples in which the automatic analysis device in FIG. 1 is modified. In an automatic analysis device 401 in FIG. 4, unlike the configuration example of FIG. 1, the reagent stirring mechanism 108 is provided on the reagent cold storage unit 104. Similarly to the case of FIG. 1, the reagent stirring mechanism 108 has a movable area including the additional reagent storage portion 111, but does not perform the access operation to the additional reagent storage portion 111 during the normal analysis operation. In an automatic analysis device 501 in FIG. 5, unlike the configuration example in FIG. 1, the reagent stirring mechanism 108 is not provided. For example, in a device that does not use magnetic particles or the like as the reagent, the reagent stirring mechanism 108 is not particularly required.

In an automatic analysis device 601 in FIG. 6, unlike the configuration example in FIG. 1, the additional reagent storage portion 111 is integrated with the reagent cold storage unit 104. As a result, it is possible to keep the additional reagent storage portion 111 at a same temperature as the reagent cold storage unit 104. Specifically, a temperature of the reagent cold storage unit 104 including a temperature of the additional reagent storage portion 111 is adjusted by, for example, an air cooling method using a heat exchanger or a water cooling method using a water cooling jacket or the like. The additional reagent storage portion 111 is provided with an additional reagent holding portion 602 for holding the additional reagent. As described above, the reagent stirring mechanism may be provided on the reagent cold storage unit 104, or the reagent stirring mechanism may not be provided.

In the automatic analysis device illustrated in FIG. 1 and FIGS. 4 to 6, the reagent dispensing mechanism 107 and the reagent stirring mechanism 108 performs the rotational movement on one rotation axis on the X-Y plane. For this reason, the additional reagent storage portion 111 needs to be disposed on a circumferential orbit of the reagent dispensing mechanism 107 and the reagent stirring mechanism 108. However, the drive mechanism for the rotational movement needs to have at least one or more rotation axes. As an example, in an automatic analysis device 701 illustrated in FIG. 7, the reagent dispensing mechanism 107 and the reagent stirring mechanism 108 have a plurality of rotation axes associated with the rotational movement. Since the movable area in this case is wider than that with only one rotation axis, a disposing location of the additional reagent storage portion 111 is not limited to a specific circumferential orbit. As a result, flexibility in determining the disposing location of the additional reagent storage portion 111 is improved.

<Main Effect of Embodiment 1>

As described above, by using the aspect of Embodiment 1, the additional reagents can be easily introduced and replaced during the operation even in a small-scale automatic analysis device. As a result, even when the reagents need to be supplied or added during the operation of the analysis device, analysis can be continued in a short time, and diagnosis and treatment based on analysis results can be implemented earlier. In addition, a reagent container transfer mechanism disclosed in PTL 2 or PTL 3 is not required, and the introduction and the replacement of the additional reagent can be performed by adjusting the movable area of the movable components and planning a storage location for the additional reagent. As a result, the device does not increase in size, and a cost can be reduced.

Embodiment 2

<Method for Using Additional Reagent Storage Portion (Application Example)>

FIG. 8 and FIG. 9 is a view illustrating an example of a method of using an additional reagent storage portion in an automatic analysis device according to Embodiment 2. In the automatic analysis device described in Embodiment 1, the additional reagent storage portion 111 stores the additional reagent container 123. On the other hand, the additional reagent storage portion (additional reagent storage area) 111 can store not only the additional reagent container 123 but also a sample container (sample container) 112 in which a sample (specimen) to be analyzed is stored.

Depending on the automatic analysis device, there may be a common area between the movable area of the sample dispensing mechanism (sample dispensing mechanism) 106 in FIG. 1 and the movable area of the reagent dispensing mechanism 107 and the reagent stirring mechanism 108. In this case, as long as the additional reagent storage portion 111 is disposed in this common area, the sample can be dispensed from the sample container 112 provided in the additional reagent storage portion 111 by the sample dispensing mechanism 106. Also, depending on the automatic analysis device, the reagent dispensing mechanism 107 may also include a sample dispensing mechanism. In this case, the sample can be dispensed from the sample container 112 by the reagent dispensing mechanism 107.

However, a size of the reagent container 113 (or the additional reagent container 123) maybe different from a size of the rack 102 accommodating the sample containers 112 as illustrated in FIG. 1. Therefore, in order to enable the rack 102 to be provided in the additional reagent storage portion 111, for example, it is useful to use a method as illustrated in FIGS. 8 and 9.

In FIG. 8, an adapter member whose bottom has a same shape as the reagent container 113 and capable of connecting with the rack 102 is used. As illustrated in FIG. 8, since a bottom of an adapter member 802 has a same structure as the reagent container 113, the adapter member 802 can be adapted to an additional reagent holding portion 801 of the additional reagent storage portion 111. Therefore, by mounting the adapter member 802 on the rack 102, the rack 102 can be provided and fixed to the additional reagent holding portion 801 via the adapter member 802. On the other hand, in FIG. 9, an additional reagent holding portion 901 has a shape that adopts both the reagent container 113 and the rack 102. In this case, the rack 102 can be directly provided on the additional reagent storage portion 111 without using the adapter member.

<Main Effect of Embodiment 2>

As described above, by using the method of Embodiment 2, same effect as that of Embodiment 1 can be obtained. In addition, in order to supply the sample during the analysis operation, for example, an interrupt measurement can be performed on an emergency specimen at an early stage.

Embodiment 3

<Overall Schematic Configuration of Automatic Analysis Device (Embodiment 3)>

FIG. 10 is a schematic view illustrating a configuration example of an automatic analysis device according to Embodiment 3. In an automatic analysis device 1001 illustrated in FIG. 10, unlike the case of Embodiment 1, a reagent dispensing mechanism 1002 and a reagent stirring mechanism 1003 perform an access operation to a normal reagent storage portion (normal reagent storage area) 1008 and an additional reagent storage portion (additional reagent storage area) 1006 by linear movement instead of the rotational movement on the X-Y plane. Although not illustrated, the automatic analysis device 1001 also includes a control portion 124 and the like similar to those in FIG. 1.

In FIG. 10, the reagent dispensing mechanism 1002 and the reagent stirring mechanism 1003 are provided on a rail that moves in X-axis, Y-axis, and Z-axis directions. Drive mechanisms thereof dispense reagents from a reagent container to a reaction container stored in the incubator disk 105. At least a part of an upper surface of a reagent cold storage unit 1004 is covered by a reagent disk cover 1005. The additional reagent storage portion 1006 in this example is provided in the reagent cold storage unit 1004 and is kept at a temperature same as that of the cold storage unit. Same as the case of Embodiment 1, the reagent dispensing mechanism 1002 and the reagent stirring mechanism 1003 do not perform the access operation to the additional reagent storage portion 1006 during a normal analysis operation, and performs the access operation to the additional reagent storage portion 1006 when a predetermined instruction is received.

The additional reagent storage portion 1006, same as the case of FIG. 1, maybe disposed outside the reagent cold storage unit 1004. In this case, an additional reagent may be kept cool by ventilating the additional reagent storage portion 1006 and the reagent cold storage unit 1004. In addition, the additional reagents may be kept cool by using a temperature adjustment mechanism (for example, a peltier element, or the like) different from the reagent cold storage unit 1004, or further, may not be kept cool. The additional reagent storage portion 1006 is provided with an additional reagent holding portion 1007 for holding the additional reagent container. At least one reagent can be added to the additional reagent storage portion 1006.

FIG. 11A is a plan view illustrating a configuration example of a cover mounted on the automatic analysis device in FIG. 10, and FIG. 11B is a perspective view of FIG. 11A. Same as the case of Embodiment 1, it is desirable that the automatic analysis device 1001 is mounted with a whole cover 1101 and an individual cover 1102 for the additional reagent storage portion 1006 that respectively have individual interlock mechanisms. As described above, this allows an introduction or a replacement of the additional reagents without stopping the analysis operation.

A method for introducing and replacing the additional reagent is also the same as that of Embodiment 1. For example, the operator may use the operation portion to notify the device of the fact, so that once in a case where the introduction or the replacement can be performed, the automatic analysis device 1001 turns into a state where the introduction or the replacement can be performed (for example, a lock release state of individual cover 1102) based on information of the device itself, regardless of whether or not the device is notified. Further, same as the case of Embodiment 1, from a viewpoint of safety, it is desirable to provide a mechanism in advance, in which a guard member that physically shields the additional reagent storage portion 1006 and the reagent cold storage unit 1004 appears at the same time when the individual cover 1102 is opened.

With respect to reagent information, it is desirable that information such as the device installation history and remaining analysis possible number of the reagent based on the reagent label 204 (FIG. 2), which are registered when the additional reagent is introduced, is taken over when the reagent is transferred from the additional reagent storage portion 1006 to the normal reagent storage portion 1008. Further, the rack accommodating the sample containers can be provided in the additional reagent storage portion 1006 by the same method as in Embodiment 2.

<Main Effect of Embodiment 3>

As described above, by using the method of Embodiment 3, the same effect as that of Embodiment 1 can be obtained. In general, a drive mechanism that performs the linear movement as illustrated in FIG. 10 is likely to cause an increase in the size of the device and an increase in the cost of the device in comparison with the drive mechanism that performs the rotational movement described in Embodiment 1. Therefore, from this viewpoint, the configuration example of FIG. 1 and the like may be more useful.

Embodiment 4

<Overall Schematic Configuration of Automatic Analysis Device (Embodiment 3)>

FIG. 12 is a schematic view illustrating a configuration example of an automatic analysis device according to Embodiment 4. In an automatic analysis device 1201 illustrated in FIG. 12, unlike the case of Embodiment 3, a reagent dispensing mechanism 1205 and a reagent stirring mechanism 1206 perform an access operation to a normal reagent storage portion (normal reagent storage area) 1209 and to an additional reagent storage portion (additional reagent storage area) 1207 by a combination of linear movement on the X-Y plane and linear movement in a vertical direction (Z-axis direction) of the plane. Although not illustrated, the automatic analysis device 1201 also includes a control portion 124 and the like similar to those in FIG. 1.

In FIG. 12, an additional reagent container 1202 and a reagent container 1204 in a reagent cold storage unit 1203 are not disposed on a same X-Y plane. The reagent dispensing mechanism 1205 and the reagent stirring mechanism 1206 do not perform the access operation to the additional reagent storage portion 1207 during a normal analysis operation, and performs the access operation to the additional reagent storage portion 1006 by being moved in the Z-axis direction via a drive mechanism when a predetermined instruction is received. The automatic analysis device 1201 illustrated in FIG. 12 includes the reagent cold storage unit 1203, the reagent container 1204, the reagent dispensing mechanism 1205, the reagent stirring mechanism 1206, the additional reagent storage portion 1207, an additional reagent holding portion 1208, and the additional reagent container 1202. However, in actuality, various mechanisms similar to those of Embodiment 3 (not illustrated) are provided in addition.

The additional reagent storage portion 1207 in this example is provided in reagent cold storage unit 1203 and is kept at a temperature same as that of the reagent cold storage unit 1203. However, as described in Embodiment 3, a location relationship between the additional reagent storage portion 1207 and the reagent cold storage unit 1203, and various methods of temperature adjustment can be appropriately changed. Also, a configuration of a cover, taking over of reagent information, and a setting of racks are same as those in Embodiment 3. At least one reagent can be added to the additional reagent storage portion 1207.

<Main Effect of Embodiment 4>

As described above, by using the method of Embodiment 4, the same effect as that of Embodiment 1 can be obtained.

Embodiment 5

<Overall Schematic Configuration of Automatic Analysis Device (Embodiment 5)>

FIG. 13 is a schematic view illustrating a configuration example of an automatic analysis device according to Embodiment 5. An automatic analysis device 1301 illustrated in FIG. 13 has two systems of a reagent cold storage unit, a reagent dispensing mechanism, and a reagent stirring mechanism. A reagent cold storage unit 1311 of a first system is provided with an additional reagent storage portion (additional reagent storage area) 1303. The first system is a system in which reagents can be added or replaced even during a normal analysis operation. On the other hand, a reagent cold storage unit 1304 of a second system is provided with a normal reagent storage portion (normal reagent storage area) 1302. The second system is a system for the normal analysis operation, and the reagents cannot be added or replaced during the normal analysis operation.

An incubator disk (reaction disk) 1306 accommodating a plurality of reaction containers 1305 is provided on an outer periphery of the reagent cold storage unit 1304 of the second system. At least one reagent can be added to both of the first system and the second system. The first system and the second system are kept cool by different temperature adjustment mechanisms. However, the first system may not be kept cool. A reagent in the reagent cold storage unit 1311 of the first system is dispensed and stirred by a reagent dispensing mechanism 1307 and a reagent stirring mechanism 1308. On the other hand, a reagent in the reagent cold storage unit 1304 of the second system is dispensed and stirred by a reagent dispensing mechanism 1309 and a reagent stirring mechanism 1310. Each of the two reagent dispensing mechanisms 1307, 1309 can freely access the reaction containers 1305 accommodated in the reaction disk 1306.

The first system (1311, 1307, and 1308) operates in parallel with the second system (1304, 1309, and 1310) during the normal analysis operation, but even during the normal analysis operation, the first system stops operating when a predetermined instruction is received. In this state, the normal analysis operation is continued only by the second system (1304, 1309, and 1310). That is, the second system (1304, 1309, and 1310) performs the normal analysis operation, regardless of whether or not the predetermined instruction is received. As a result, it is possible to construct a state where the first system stops operating while the normal analysis operation is continued, and therefore, even during the normal analysis operation, the reagents can be added or replaced to the additional reagent storage portion 1303.

In the example of FIG. 13, since the first system does not reach a movable area 1312 of the reagent dispensing mechanism 1309 and the reagent stirring mechanism 1310 of the second system, as long as the first system stops operating, the reagents can be added or replaced to the additional reagent storage portion 1303. However, it is conceivable that depending on the automatic analysis device, the first system may reach the movable area 1312 of the reagent dispensing mechanism 1309 and the reagent stirring mechanism 1310 of the second system. Based on this viewpoint, the additional reagent storage portion 1303 needs to be disposed within a movable area 1313 of the reagent dispensing mechanism 1307 and the reagent stirring mechanism 1308 of the first system, and in an area excluding the movable area 1312 of the reagent dispensing mechanism 1309 and the reagent stirring mechanism 1310 of the second system.

FIG. 14A is a plan view illustrating a configuration example of a cover mounted on the automatic analysis device in FIG. 13, and FIG. 14B is a perspective view of FIG. 14A. Same as the case of Embodiment 1, it is desirable that the automatic analysis device 1301 is mounted with a whole cover 1401 and an individual cover 1402 for the additional reagent storage portion 1303 that respectively have individual interlock mechanisms. As a result, this allows an introduction or a replacement of the additional reagents without stopping the analysis operation.

A method for introducing and replacing the additional reagent is also the same as that of Embodiment 1. For example, the operator may use the operation portion to notify the device of the fact, so that once in a case where the introduction or the replacement can be performed, the automatic analysis device 1301 turns into a state where the introduction or the replacement can be performed (for example, a lock release state of individual cover 1402) based on information of the device itself, regardless of whether or not the device is notified. Specifically, the latter case includes, for example, a case where one of the reagents stored in the reagent cold storage unit 1304 of the second system is predicted to be completely consumed, and a case where a reagent corresponding to an analysis item registered in the device is not provided.

Further, same as the case of Embodiment 1, from a viewpoint of safety, it is desirable to provide a mechanism in advance, in which a guard member that physically shields the first system and the second system appears at the same time when the individual cover 1402 is opened. With respect to the reagent information, it is desirable that information such as the device installation history and remaining analysis possible number of the reagent based on the reagent label 204 (FIG. 2), which are registered when the additional reagent is introduced, is taken over when the reagent is transferred from the additional reagent storage portion 1303 to the normal reagent storage portion 1302.

FIG. 15A and FIG. 15B are schematic views illustrating a configuration example of a guard member. FIG. 15A illustrates a planar configuration example of the automatic analysis device 1301 in a state where the individual cover 1402 is closed, and a cross-sectional configuration example between line A-A' thereof. In FIG. 15A, a plate-shaped guard member 1501 is provided at a lower part in the automatic analysis device 1301 with a unit mounting surface 1502 being interposed. The guard member 1501 is provided so as to be located at a lower part on a side of the reagent cold storage unit 1304 on the individual cover 1402. In other words, the guard member 1501 is provided at a boundary line between the reagent cold storage unit 1311 of the first system and the reagent cold storage unit 1304 of the second system and at the lower part with the unit mounting surface being interposed.

FIG. 15B illustrates a planar configuration example of the automatic analysis device 1301 in a state of the individual cover 1402 being opened, and a cross-sectional configuration example between line B-B' thereof. As illustrated in FIG. 15B, when the individual cover 1402 is opened, the guard member 1501 appears at an upper part with the unit mounting surface 502 being interposed in conjunction therewith. As a result, the first system and the second system are physically shielded by the guard member 1501 at the upper part with the unit mounting surface 502 being interposed. Here, the plate-shaped guard member 1501 is used, but, for example, a guard member that opens and closes in a fan shape may also be used.

<Overall Schematic Configuration of Automatic Analysis Device (Various Modifications)>

FIGS. 16 and 17 are schematic views respectively illustrating various configuration examples in which the automatic analysis device in FIG. 13 is modified. In an automatic analysis device 1601 in FIG. 16, unlike the configuration example of FIG. 13 but same as the case of FIG. 4, the reagent stirring mechanisms 1308, 1310 are respectively provided on the reagent cold storage units 1311, 1304. In an automatic analysis device 1701 in FIG. 17, unlike the configuration example of FIG. 13 but same as the case of FIG. 5, the reagent stirring mechanisms 1308, 1310 are not provided.

<Main Effect of Embodiment 5>

As described above, by using the method of Embodiment 5, the same effect as that of Embodiment 1 can be obtained. Further, by having two systems of a reagent cold storage unit, a reagent dispensing mechanism and a reagent stirring mechanism, the normal analysis operation can be performed more efficiently, and further, the introduction or the replacement of additional reagents can be performed while the normal analysis operation is continued. Further, the additional reagent storage portion 1303 can be used not only as an area dedicated to the additional reagent as in Embodiment 1 but also as an area for the normal analysis operation, so that a space can be used more efficiently.

While the invention made by the present inventors has been specifically described based on the embodiments, the invention is not limited to the embodiments described above, and various changes and modifications may be made without departing from the scope of the invention. For example, the embodiments described above have been described in detail for easy understanding of the invention, but the invention is not necessarily limited to those including all the configurations described above. Apart of the configuration of one embodiment can be replaced with the configuration of another embodiment, and the configuration of another embodiment can be added to the configuration of one embodiment. In addition, it is possible to add, delete, and replace other configurations for a part of the configuration of each embodiment.

REFERENCE SIGNS LIST

101: automatic analysis device, 102: specimen rack, 103: rack transport line, 104: reagent cold storage unit, 105: incubator disk, 106: sample dispensing mechanism, 107: reagent dispensing mechanism, 108: reagent stirring mechanism, 109: expendable item transport unit, 110: detection portion unit, 111: additional reagent storage portion, 112: sample container, 113: reagent container, 114: reagent disk cover, 115: reaction container, 116: reaction container disposition portion, 117: expendable item accommodation container, 118: accommodation container holding portion, 119: transport mechanism, 120: disposal hole, 121: dispensing tip, 122: chip mounting position, 123: additional reagent container, 130: normal reagent storage portion, 131: movable area, 132: normal movable area, 204: reagent label, 205: reading portion, 301: whole cover, 302: individual cover, 602: additional reagent holding portion, 801: additional reagent holding portion, 802: adapter member, 901: additional reagent holding portion, 1002: reagent dispensing mechanism, 1004: reagent cold storage unit, 1006: additional reagent storage unit, 1007: additional reagent holding portion, 1008: normal reagent storage portion, 1101: whole cover, 1102: individual cover, 1202: additional reagent container, 1203: reagent cold storage unit, 1204: reagent container, 1205: reagent dispensing mechanism, 1207: additional reagent storage portion, 1208: additional reagent holding portion, 1302: normal reagent storage portion, 1303: additional reagent storage portion, 1304: reagent cold storage unit, 1305: reaction container, 1306: incubator disk, 1307: reagent dispensing mechanism, 1309: reagent dispensing mechanism, 1311: reagent cold storage unit, 1312: movable area, 1313: movable area, 1401: whole cover, 1402: individual cover, 1501: guard member, 1601: automatic analysis device, 1701: automatic analysis device

The invention claimed is:

1. An automatic analysis device comprising:
a dispensing mechanism comprising a rotary drive and a translational drive and configured to dispense a reagent from a plurality of reagent containers in which a reagent is stored;
a first storage area located in a first movable area which is a normal movable area disposed along a first portion of a circumferential orbit of the dispensing mechanism in an X-Y plane, and in which a first reagent container of the plurality of reagent containers is disposed; and
a second storage area located in a second movable area which is an additional movable area other than the normal movable area disposed along a second portion of the circumferential orbit of the dispensing mechanism in the X-Y plane, and in which a second reagent container of the plurality of reagent containers is disposed, wherein
the dispensing mechanism performs an access operation in the normal movable area in response to a normal operation being performed, and performs an access operation to the second storage area in response to receiving a predetermined instruction from a control computer,
the second storage area is accessible by a user while the dispensing mechanism performs the access operation in the normal movable area,
the control computer is configured to issue the predetermined instruction after the user accesses the second storage area, and
the second storage area is constructed to provide a container placement position at which both the second reagent container and a sample container storing a sample to be analyzed are able to be placed.

2. The automatic analysis device according to claim 1, further comprising:
an adapter disposed at the container placement position and configured such that the second reagent container and the sample container are able to be mounted together.

3. The automatic analysis device according to claim 2, wherein
the container placement position is configured to be compatible with the second reagent container and the sample container.

4. The automatic analysis device according to claim 1, further comprising:
a whole cover that prevents a manual operation from being performed on the automatic analysis device during the analysis operation, and operates a predetermined safety function in response to opening and closing; and
an individual cover which is an exit-entrance for a manual operation performed on the second storage area, and which is configured to be opened and closed in response to the whole cower being closed, and does not operate the predetermined safety function.

5. The automatic analysis device according to claim 4, further comprising:
a guard member including a mechanism that is ableconfigured to switch between a-first and second states for respectively shielding and not shielding the second storage area from other areas, and to physically prevent the access operation to the second storage area in the second state in which the second storage area is shielded from other areas.

6. The automatic analysis device according to claim 1, wherein
whether or not the access operation to the second storage area is performed is changeable based on information stored in the automatic analysis device.

7. The automatic analysis device according to claim 6, wherein
the information stored in the automatic analysis device is-comprises at least one of the following: information indicating that a remaining amount of at least one of reagent is dropped to a certain value or less; information indicating that the reagent corresponding to an analysis requested item registered in the automatic analysis device is unusable; and information indicating that an additional reagent is provided in the second storage area.

8. The automatic analysis device according to claim 4, wherein
whether or not the access operation to the second storage area is performed is changeable based on information stored in the automatic analysis device.

9. The automatic analysis device according to claim 8, wherein
the information stored in the automatic analysis device is at least one of information indicating that the individual cover is opened, and information indicating that a lock of the individual cover is released.

10. The automatic analysis device according to claim 4, wherein
the control computer is configured to release a lock of the individual cover based on associated information stored in the automatic analysis device.

11. The automatic analysis device according to claim 1, further comprising:
a temperature adjustment mechanism configured to commonly control temperatures of the first storage area and the second storage area.

12. The automatic analysis device according to claim 1, further comprising:
a first temperature adjustment mechanism configured to control a temperature of the first storage area; and
a second temperature adjustment mechanism configured to control a temperature of the second storage area.

13. The automatic analysis device according to claim 1, wherein
each said reagent container includes a label indicating information on a reagent contained therein, and the automatic analysis device further comprises one or more reading portions configured to read the label of the reagent containers stored in the first storage area and the second storage area.

14. The automatic analysis device according to claim 13, wherein
the information on the reagent is at least one of information indicating presence or absence of a history of the reagent container being provided in the automatic analysis device, and information indicating a remaining analysis possible number in the reagent container.

15. The automatic analysis device according to claim 1, wherein
the dispensing mechanism is configured to perform an access operation to the first storage area and the second storage area by rotational movement on a plane.

16. The automatic analysis device according to claim 15, wherein
the dispensing mechanism includes a plurality of rotation axes associated with the rotational movement.

17. The automatic analysis device according to claim 1, wherein
the dispensing mechanism is configured to perform an access operation to the first storage area and the second storage area by linear movement on the X-Y plane.

18. The automatic analysis device according to claim 1, wherein
the dispensing mechanism is configured to perform an access operation to the first storage area and the second storage area by a combination of linear movement on the X-Y plane and linear movement in a vertical direction with respect to the X-Y plane.

19. The automatic analysis device according to claim 1, further comprising:
at least two pairs of combinations of the first storage area and the dispensing mechanism that performs the access operation to the first storage area.

* * * * *

UNITED STATES PATENT AND TRADEMARK OFFICE
CERTIFICATE OF CORRECTION

| | |
|---|---|
| PATENT NO. | : 11,639,943 B2 |
| APPLICATION NO. | : 16/641349 |
| DATED | : May 2, 2023 |
| INVENTOR(S) | : Kenta Imai et al. |

It is certified that error appears in the above-identified patent and that said Letters Patent is hereby corrected as shown below:

In the Claims

At Column 18, Claim number 5, Lines 40-41, please change "that is ableconfigured to switch between a-first and second" to -- configured to switch between first and second --

At Column 18, Claim number 7, Line 55, please change "is-comprises" to -- comprises --

Signed and Sealed this
Nineteenth Day of September, 2023

Katherine Kelly Vidal
*Director of the United States Patent and Trademark Office*